US009995766B2

(12) United States Patent
Reed et al.

(10) Patent No.: US 9,995,766 B2
(45) Date of Patent: Jun. 12, 2018

(54) METHODS AND SYSTEMS FOR MEASURING A PROPERTY OF A MACROMOLECULE

(75) Inventors: Jason C. Reed, Santa Monica, CA (US); Bhubaneswar Mishra, Great Neck, NY (US); Andrew Sundstrom, Brooklyn, NY (US)

(73) Assignee: The Regents of the University of California, Oakland, CA (US)

( * ) Notice: Subject to any disclaimer, the term of this patent is extended or adjusted under 35 U.S.C. 154(b) by 900 days.

(21) Appl. No.: 12/817,004

(22) Filed: Jun. 16, 2010

(65) Prior Publication Data

US 2011/0013820 A1   Jan. 20, 2011

Related U.S. Application Data

(60) Provisional application No. 61/187,570, filed on Jun. 16, 2009.

(51) Int. Cl.
| | |
|---|---|
| *G06K 9/00* | (2006.01) |
| *G01Q 30/04* | (2010.01) |
| *B82Y 35/00* | (2011.01) |
| *C12Q 1/68* | (2018.01) |
| *G06T 7/60* | (2017.01) |
| *G06F 19/16* | (2011.01) |
| *G06F 19/24* | (2011.01) |

(52) U.S. Cl.
CPC .............. *G01Q 30/04* (2013.01); *B82Y 35/00* (2013.01); *C12Q 1/68* (2013.01); *G06T 7/60* (2013.01); *G06F 19/16* (2013.01); *G06F 19/24* (2013.01); *G06T 2207/10024* (2013.01); *G06T 2207/20036* (2013.01); *G06T 2207/20072* (2013.01); *G06T 2207/30004* (2013.01)

(58) Field of Classification Search
CPC ..................................................... B82Y 35/00
USPC ......................................................... 382/133
See application file for complete search history.

(56) References Cited

U.S. PATENT DOCUMENTS

| | | | | |
|---|---|---|---|---|
| 4,768,143 A | * | 8/1988 | Lane .................... | G05B 13/044 700/37 |
| 5,644,512 A | * | 7/1997 | Chernoff ............... | G01Q 40/00 310/317 |
| 6,141,461 A | * | 10/2000 | Carlini .................... | G06T 5/20 382/261 |
| 6,294,136 B1 | * | 9/2001 | Schwartz .................... | 422/186 |
| 6,365,353 B1 | * | 4/2002 | Lorch et al. ............... | 435/6.11 |
| 6,591,658 B1 | * | 7/2003 | Yedur et al. ............... | 73/1.89 |

(Continued)

OTHER PUBLICATIONS

Reed et al. A quantitative study of optical mapping surfaces by atomic force microscopy and restriction endonuclease digestion assays. (1998) Anal. Biochem. 259:80-88.

(Continued)

*Primary Examiner* — Lena Najarian
*Assistant Examiner* — Trang T Nguyen
(74) *Attorney, Agent, or Firm* — Bozicevic Field & Francis, LLP; Paula A. Borden; Rudy J. Ng

(57) ABSTRACT

The present disclosure provides methods of measuring a property of a macromolecule. The methods generally involve applying an empirically learned correction term to a test metric to generate a high-accuracy measurement. The present disclosure further provides a computer program product and a computer system for carrying out a subject method.

15 Claims, 17 Drawing Sheets

(56) References Cited

U.S. PATENT DOCUMENTS

| | | | |
|---|---|---|---|
| 6,998,228 B2* | 2/2006 | Henderson | C12Q 1/6834 435/4 |
| 8,050,802 B2* | 11/2011 | Young | B82Y 35/00 250/442.11 |
| 8,262,879 B2* | 9/2012 | Oliver | 204/450 |
| 2003/0130823 A1* | 7/2003 | Potyrailo | G01J 3/28 702/189 |
| 2003/0172043 A1* | 9/2003 | Guyon et al. | 706/48 |
| 2004/0248134 A1* | 12/2004 | Sperling et al. | 435/6 |
| 2005/0042623 A1* | 2/2005 | Ault-Riche et al. | 435/6 |
| 2005/0042668 A1* | 2/2005 | Perlin | 435/6 |
| 2005/0086010 A1* | 4/2005 | Rao et al. | 702/20 |
| 2005/0158790 A1* | 7/2005 | Mei | C12Q 1/6813 435/6.18 |
| 2006/0216814 A1* | 9/2006 | Kobayashi et al. | 435/287.2 |
| 2007/0092905 A1* | 4/2007 | Gimzewski | C12Q 1/683 435/6.16 |
| 2007/0134656 A1* | 6/2007 | Sharma et al. | 435/6 |
| 2008/0009434 A1* | 1/2008 | Reches | A61L 27/38 530/300 |
| 2008/0089568 A1* | 4/2008 | Delenstarr | G01N 21/253 382/128 |
| 2008/0242556 A1* | 10/2008 | Cao et al. | 506/9 |
| 2010/0078325 A1* | 4/2010 | Oliver | 204/452 |
| 2010/0122385 A1* | 5/2010 | Hu et al. | 850/5 |

OTHER PUBLICATIONS

Andrew Sundstrom, Masters Thesis, New York University, Oct. 24, 2008.

* cited by examiner

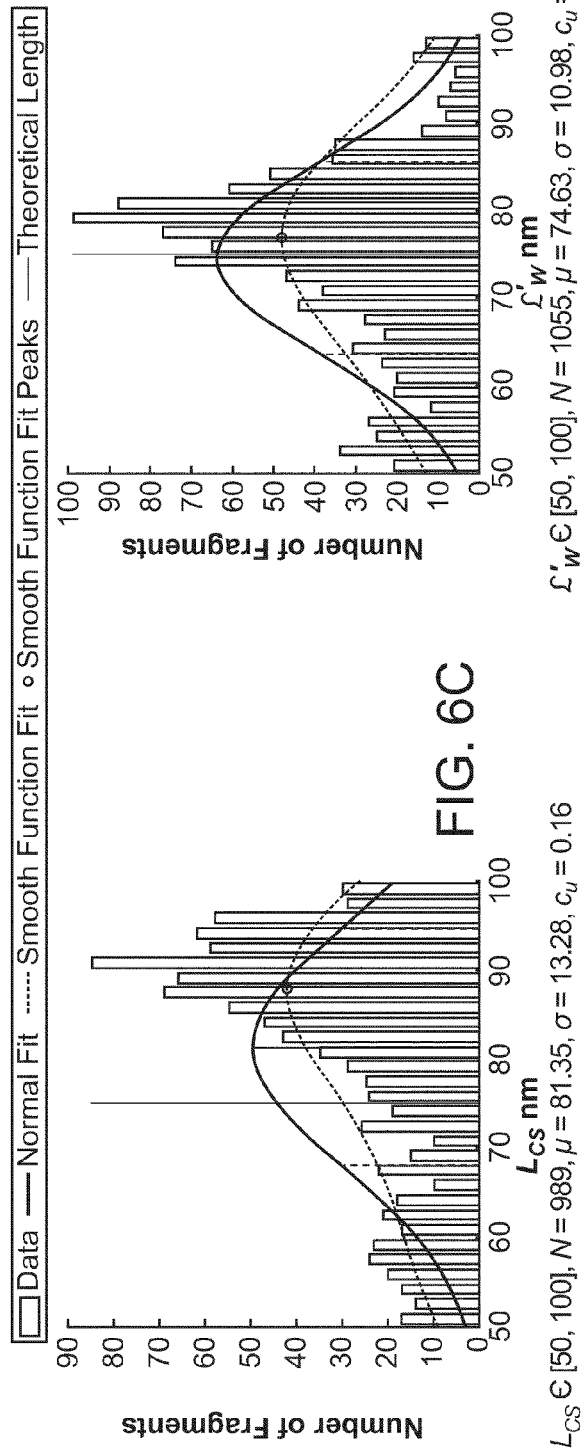
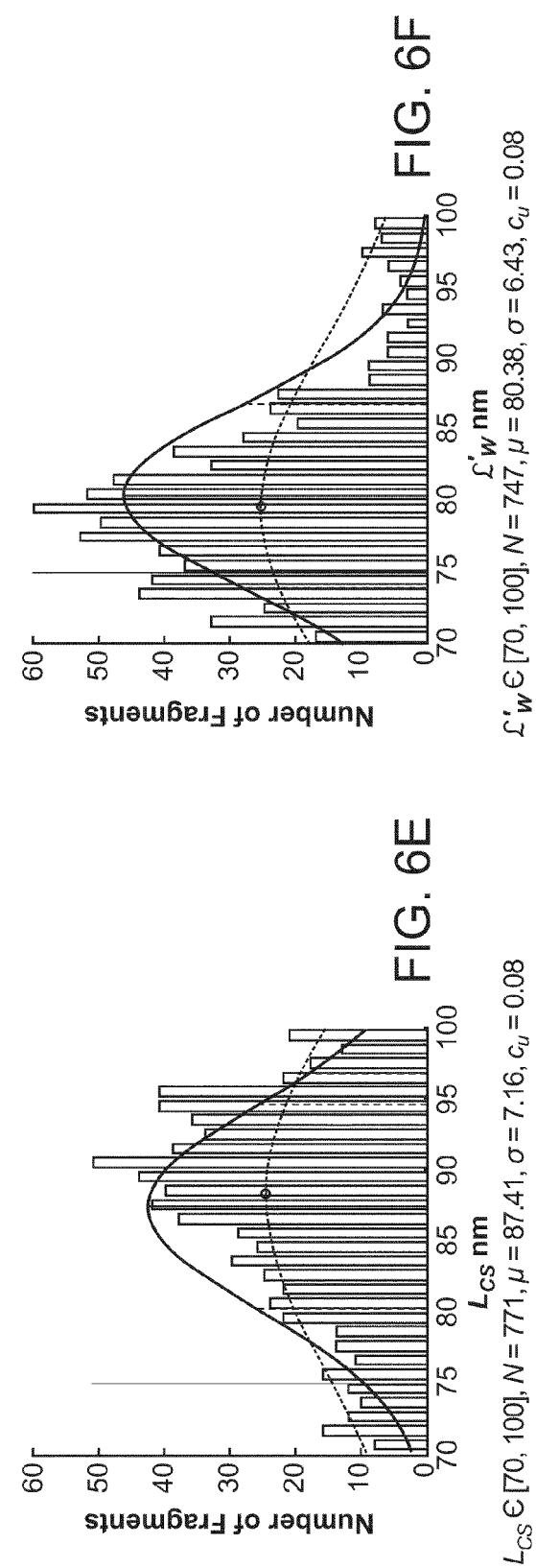
FIG. 6C
FIG. 6D
FIG. 6E
FIG. 6F

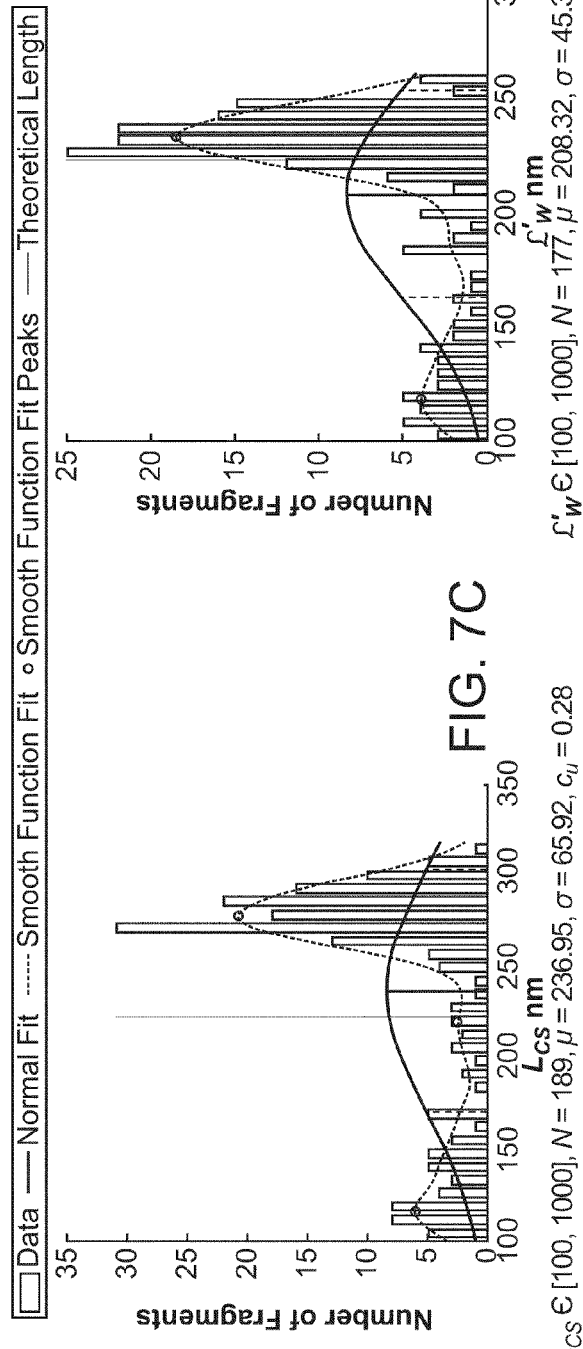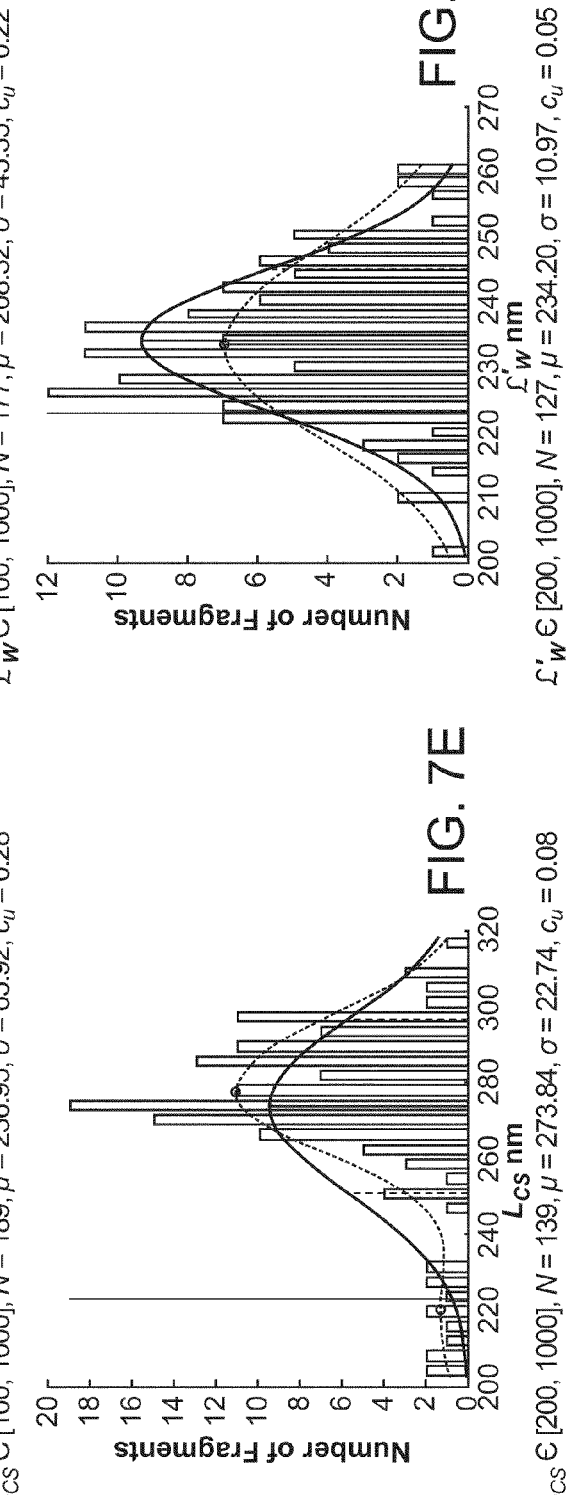

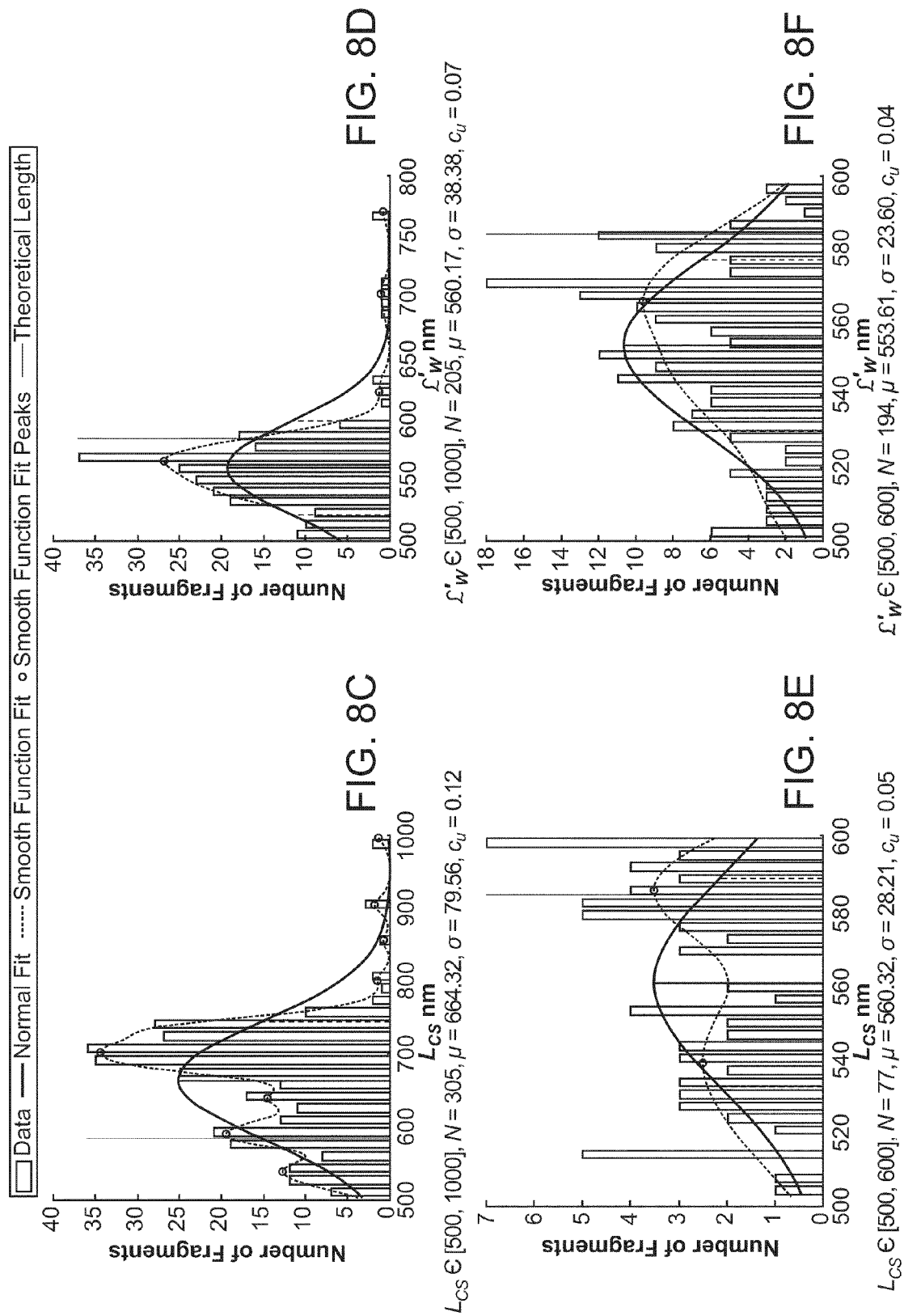

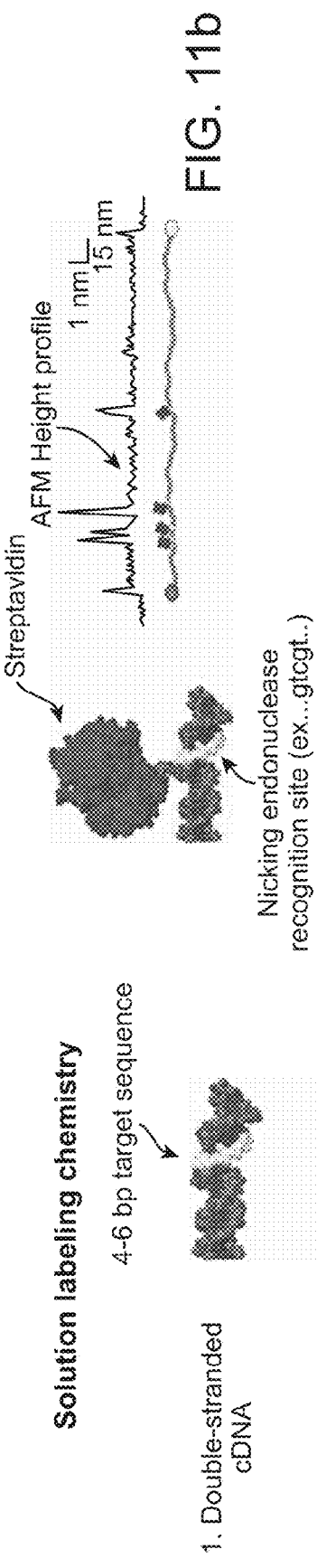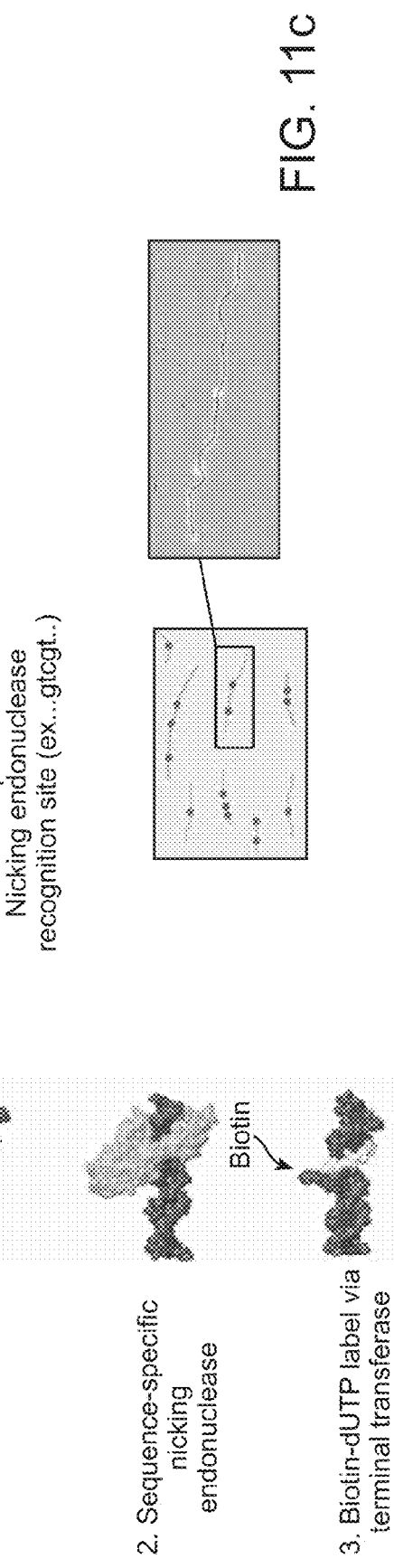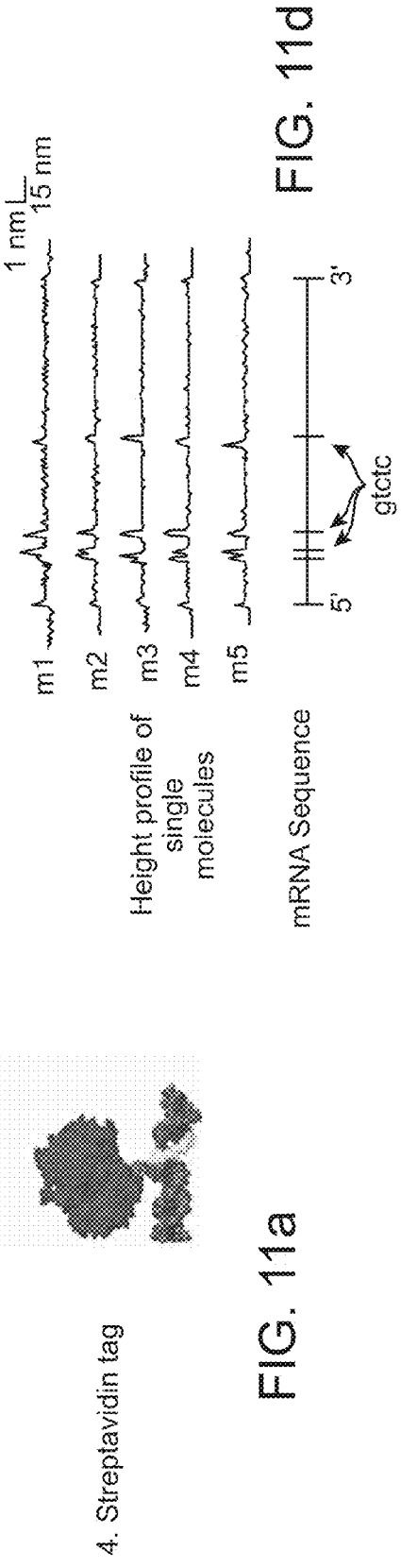

$$\text{Odds Ratio} = \frac{p(\text{sequence}_n \mid \text{molecule}_k)}{p(\text{sequence}_m \mid \text{molecule}_k)}$$

METHODS AND SYSTEMS FOR MEASURING A PROPERTY OF A MACROMOLECULE

CROSS-REFERENCE

This application claims the benefit of U.S. Provisional Patent Application No. 61/187,570, filed Jun. 16, 2009, which application is incorporated herein by reference in its entirety.

STATEMENT REGARDING FEDERALLY SPONSORED RESEARCH

This invention was made with government support under Grant No. GM080999 awarded by the National Institutes of Health. The government has certain rights in the invention.

BACKGROUND

There are many examples of problems in pattern analysis for which it is often possible to obtain systematic characterizations, if in addition a small number of useful features or parameters of the image are known a priori or can be estimated. Solution of an image-processing algorithm applied to such problems could suffer from inaccuracies.

LITERATURE

Reed et al. (1998) *Anal. Biochem.* 259:80-88; U.S. Patent Publication No. 2007/0092905.

SUMMARY OF THE INVENTION

The present disclosure provides methods of measuring a property of a macromolecule. The methods generally involve applying an empirically learned correction term to a test metric to generate a high-accuracy measurement. The present disclosure further provides a computer program product and a computer system for carrying out a subject method.

BRIEF DESCRIPTION OF THE DRAWINGS

FIGS. 6A-F depict distributions of $L_{CS}$ (left column) and $L'_W$ (right column) for Test Knowns in narrowing length regimes.

FIGS. 7A-F depict distributions of $L_{CS}$ (left column) and $L'_W$ (right column) for Test Unknowns A in narrowing length regimes.

FIGS. 8A-F depict distributions of $L_{CS}$ (left column) and $L'_W$ (right column) for Test Unknowns B in narrowing length regimes.

FIGS. 11A-D depict identifying feature pattern detection in cDNAs.

DEFINITIONS

Figure 1:
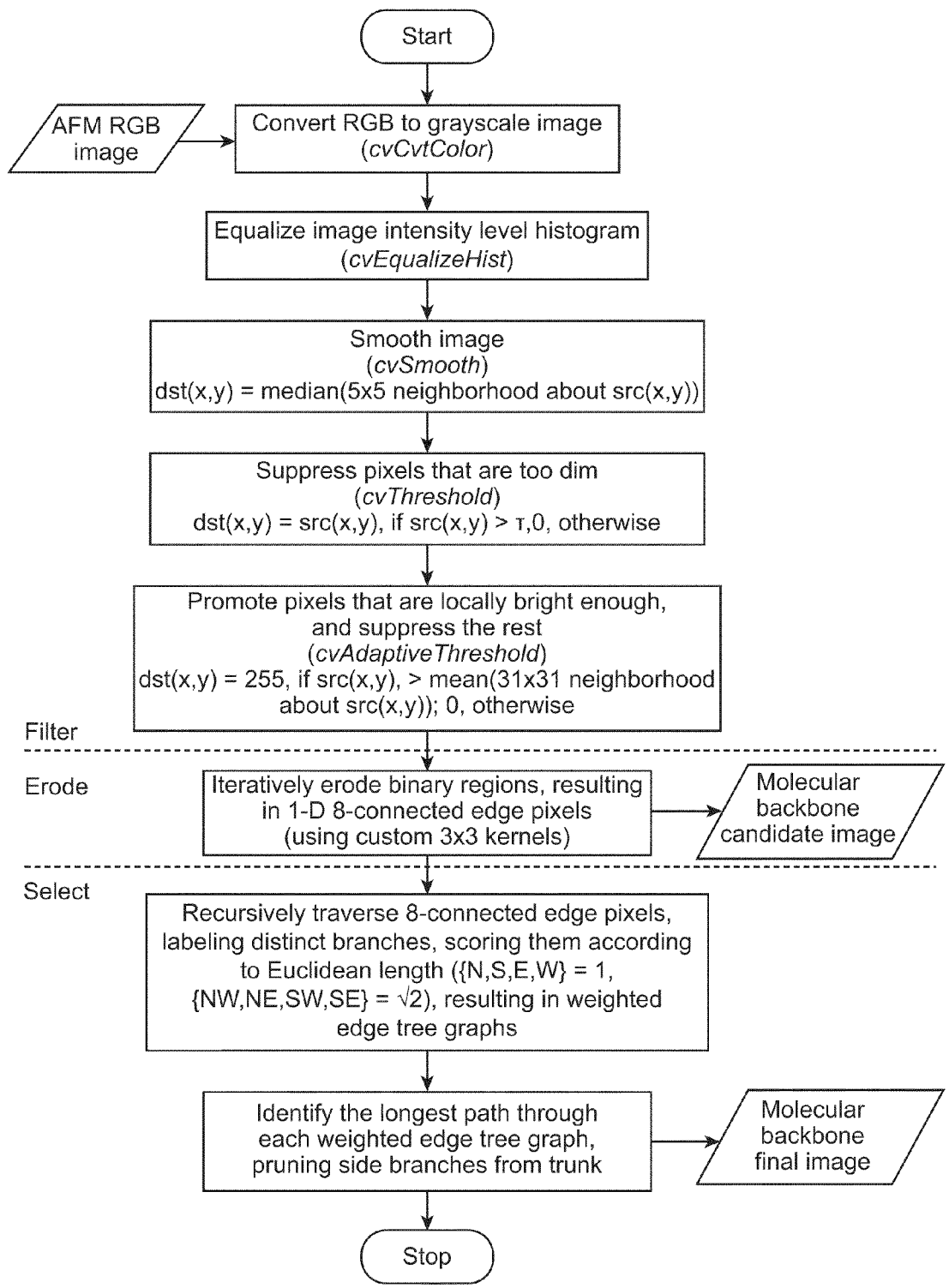
FIG. 1 depicts the AFM Explorer image processing pipeline.

A "biopolymer" refers to a polymer that is: 1) a naturally-occurring polymer present in a living cell and/or produced by a living cell; 2) a synthetic polymer that shares structural and/or sequence features with a naturally-occurring polymer. Biopolymers include nucleic acids (e.g., mRNA, cDNA, DNA, siRNA, shRNA, miRNA, etc.) and polypeptides (including translationally modified polypeptides, such as polypeptides post-translationally modified by glycosylation, phosphorylation, myristoylation, and the like).

As used herein, "nucleic acid" refers to a nucleotide polymer of any length, and includes mRNA, cDNA, DNA, siRNA, miRNA, and the like. A nucleic acid can be single-stranded or double-stranded, and can include chemical modifications. Modifications include, but are not limited to, those which provide other chemical groups that incorporate additional charge, polarizability, hydrogen bonding, electrostatic interaction, and functionality to the nucleic acid. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

Nucleic acids include, but are not limited to, genomic DNA; complementary DNA (cDNA; e.g., a reverse-transcribed copy of an mRNA); ribosomal RNA; short interfering RNA (siRNA); a ribozyme; transfer RNA (tRNA); spliced mRNA; a cDNA copy of a splice mRNA; unspliced mRNA; a cDNA copy of an unspliced mRNA; and the like. Nucleic acids include naturally-occurring nucleic acids; synthetic nucleic acids; recombinant nucleic acids; and the like.

As used herein, the term "$T_m$" refers to the melting temperature of a nucleic acid duplex at which half of the duplexes remain hybridized and half of the duplexes dissociate into single strands. The $T_m$ of a nucleic acid duplex may be experimentally determined or predicted using the following formula $T_m=81.5+16.6(\log_{10} [Na^+])+0.41$ (fraction G+C) minus (60/N), where N is the length of the nucleic acid and $[Na^+]$ is less than 1 M. See Sambrook and Russell (2001; Molecular Cloning: A Laboratory Manual, 3rd ed., Cold Spring Harbor Press, Cold Spring Harbor N.Y., chapter 10). Other formulas for predicting $T_m$ of nucleic acid duplexes exist and one formula may be more or less appropriate for a given condition or set of conditions.

The term "biological sample" encompasses a variety of sample types obtained from an organism and can be used in a diagnostic method. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components (e.g., nucleic acids, e.g., genomic DNA, mRNA, etc.). The term encompasses a clinical sample, and also includes cells in cell culture, cell supernatants, cell lysates, serum, plasma, biological fluids, and tissue samples.

The terms "body fluid" and "bodily fluid," used interchangeably herein, refer to a biological sample of liquid from an animal, e.g., a mammal, e.g., a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts. Exemplary bodily fluids of interest include those that contain nucleic acids.

By "clinical assay" is meant an assay or test that is performed on a sample obtained from an individual or patient (also referred to herein as host or subject) in order to provide information on current or future health or condition, diagnosis, treatment, prevention, and/or monitoring of a condition of the individual or patient.

A "computer-based system" refers to the hardware means, software means, and data storage means used to analyze information. The minimum hardware of a subject computer-based system comprises a central processing unit (CPU), input means, output means, data storage means, access to the Internet and data available therein. A skilled artisan can readily appreciate that any one of the currently available computer-based system are suitable for use in the present disclosure. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" or "computer" or "computing device" references any hardware and/or software combination that will perform the functions required of it. For example, any processor herein may be a programmable digital microprocessor such as available in the form of an electronic controller, mainframe, server, parallel computer, cluster computer, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a nucleic acid" includes a plurality of such nucleic acids and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides an image processing method of obtaining a high-accuracy metric (e.g., measurement) of a feature (property) of an object. The methods generally involve applying an empirically learned correction term (e.g., a set of weighted correction factors) to a test metric to generate a metric having an accuracy of greater than about 80%. The present disclosure further provides a computer program product and a computer system for carrying out a subject method.

Image Processing Method

A subject method generally involves applying an empirically learned correction term (e.g., a set of weighted correction factors) to a test metric (e.g., test measurement; where "test measurement" is also referred to herein as an "estimated measurement"), to generate a high-accuracy metric (e.g., high-accuracy measurement; where "high-accuracy measurement" is also referred to herein as a "calculated measurement" or a "computed measurement" or a "corrected measurement") that has an accuracy of greater than about 80%, greater than about 85%, greater than about 90%, greater than about 95%, greater than about 98%, or greater than about 99%, e.g., the metric has an error of less than about 20%, less than about 15%, less than about 10%, less than about 5%, less than about 2%, or less than about 1%. In some embodiments, a subject method yields a measurement having a coefficient of variation of from about 6% to about 10%, from about 4% to about 6%, from about 2% to about 4%. In some embodiments, a subject method yields a measurement having a coefficient of variation of 2%, or less than 2%.

A test measurement includes any feature of an object that can be measured. Exemplary, non-limiting measurements include length, volume, intensity, color, etc. Non-limiting examples of measurements in connection with a biopolymer include, e.g., length, the presence of post-translational modifications (e.g., glycosylation, phosphorylation, etc.), methylation, amino acid sequence, nucleic acid sequence, and the like.

A test measurement is obtained in any conventional manner or other suitable standard model. A test measurement is obtained from an image, e.g., an optical image, a scanning probe microscopy (SPM) image (e.g., atomic force microscopic image), an interferometry image, a nanoscale sensor image, and the like. In some embodiments, the image is an atomic force microscopy (AFM) image. As one non-limiting example, a biopolymer can be imaged using AFM, where an image of the biopolymer is generated. Methods of obtaining other test measurements are well known in the art.

Where the imaging method is AFM, the AFM probe contacts the macromolecule, e.g., a nucleic acid. Methods of generating an AFM image of a nucleic acid are described in, e.g., U.S. Patent Publication No. 2007/0092905. In some embodiments, the nucleic acid-contacting end of the AFM probe is functionalized to modify the attractive force between the AFM probe and the nucleic acid. In some embodiments, an external electrical current is applied to the AFM probe, generating an electrostatic potential at the nucleic acid-contacting end of the AFM probe.

In some embodiments, the amplitude of oscillation of the AFM probe is less than 10 nm, e.g., in some embodiments, the amplitude of oscillation of the AFM probe is in a range of from about 5 nm to about 10 nm, from about 1 nm to about 5 nm, from about 0.1 nm to about 1 nm, or less than about 0.1 nm. In some embodiments, the frequency of oscillation of the AFM probe is greater than about 1 megahertz (MHz), e.g., in some embodiments, the frequency of oscillation of the AFM probe is from about 1 MHz to about 5 MHz, from about 5 MHz to about 10 MHz, or greater than 10 MHz.

As noted above, in some embodiments, the nucleic acid-contacting end of the AFM probe is functionalized to modify the attractive force between the AFM probe and an immobilized nucleic acid. For example, in some embodiments, the nucleic acid-contacting end of the AFM probe is functionalized with an antibody (e.g., an antibody that specifically binds a nucleic acid, a particular feature within a nucleic acid, or a protein that is bound to a nucleic acid); a hydrophilic group; a hydrophobic group; a group comprising an electrostatic charge; a probe nucleic acid that hybridizes to a portion of the nucleic acid being measured; a protein (e.g., a protein that binds the nucleic acid; a protein that binds a non-nucleic acid moiety bound to the nucleic acid); a dye (e.g., an intercalating dye); a crystalline material; or a magnetic material. Magnetic materials include, e.g., iron oxide; nickel; cobalt; alloys comprising iron, nickel, or cobalt; and the like.

An empirically learned correction term is generated by calibrating an object of known metric. Correction factors are applied to a known metric (e.g., the length of a nucleic acid of known length; e.g., a "calibration metric") of an object (e.g., a standardized object such as a nucleic acid of known length), resulting in an empirically learned correction term, which can be, e.g., a set of weighted factors. The empirically learned correction term is then applied to the test metric, resulting in a final, high-accuracy metric of the object.

A subject image processing method can comprise the following steps: 1) a training step, in which a calibration molecule(s) is(are) used to provide a correction term (using a set of correction coefficients); 2) application of the correction term to a test measurement (an "estimated measurement") of a macromolecule present in an image. Application of the correction term to a test measurement of a macromolecule results in a high-accuracy measurement of a property of the macromolecule. A subject method involves supervised learning. Supervised learning uses a training algorithm implementing some optimization techniques which are applied to change the weights or values to provide an accurate measurement.

The training step involves generating a training set of correction coefficients, and using the set of correction coefficients to generate a correction term. The training set of correction coefficients is generated using a calibration molecules (e.g., nucleic acids of known length). Supervised learning is used to reduce bias in features applied to a set of calibration molecules (e.g., a monodisperse set of calibration molecules; e.g., a set of nucleic acids of known length), so as to eliminate features that are less likely, when applied to a test measurement, to yield a high-accuracy measurement. In other words, a subject image processing method comprises a training step in which bias in features applied to a standard model is reduced by supervised learning. The training set of correction coefficients can be reduced by shrinkage, e.g., to eliminate one or more correction coefficients. Individual correction coefficients in the training set can be weighted. The training step provides a (final) set of correction coefficients that can be used to determine a correction term. Thus, the training step generates an empirically learned correction term. The training step can be carried out with a computer.

Suitable features include, but are not limited to: a) features relating to pixellation, such as: i) the number of horizontal pixel pairs; ii) the number of vertical pixel pairs; iii) the number of diagonal pixel pairs; iv) the number of perpendicular pixel pairs; and v) the mean backbone thickness; b) features relating to the shape of a macromolecule, e.g., secondary structure of a nucleic acid, the presence of A DNA, Z DNA, height of a nucleic acid, thickness of a nucleic acid, contour of a nucleic; c) where the macromolecule is a nucleic acid, the melting temperature of a nucleic acid duplex; d) mechanical features of a macromolecule, e.g., stiffness properties, adhesive properties, etc.; e) features relating to interactions between a nucleic acid and the AFM probe; and f) the presence of counterions, which counterions may affect one or more other features such as secondary structure.

In some embodiments, shrinkage is performed on the training set of correction coefficients to eliminate coefficient terms from the training set, where coefficient terms to be eliminated include those introducing too much variance (systemic error) and/or too much dependence (model error). Shrinkage eliminates features that lead to statistical overfitting. Shrinkage produces a modified correction coefficient (biased estimator). As an example, Stein shrinkage can be applied to the correction coefficient produced by the training step. W. James and C. Stein. Estimation with quadratic loss. In Proc. Berkeley Symp. Math. Stat. Prob., pages 316-379, 1961.

In some embodiment, one or more correction coefficients can be weighted, e.g., by a false discovery rate control. False discovery control can be based on empirical Bayes methods.

Once the correction term is obtained, the correction term is applied to a test measurement of a property, e.g., an estimated measurement of a property obtained from an image. Application of the correction term to a test measurement generates a high-accuracy measurement.

As an example, one starts with a plurality of images of a nucleic acid of known length. Regression analysis is applied, to correlate a polynomial function that provides a best length estimate. Because the length of the nucleic acid is known, the system of equations can be solved, generating coefficients. These same polynomials with the same coefficients, can be applied to an image of a nucleic acid of unknown length. However, some of those coefficients may not be informative. Where a coefficient is not informative, it will be small, and can be eliminated. The initial set of coefficients is referred to as the training set. Depending upon how comprehensive the training set is, overfitting may be generated. For example, overfitting can occur if a regression analysis is being performed on a small data set, and the number of coefficients in the model is large. The model can typically be fit very precisely to the dataset; however, if overfitting occurs, the model will not be generalizable to other unknowns. Therefore, where the data set is small, a suitable approach would be to try a number of different coefficients and figure out which coefficients are the best ones, so as to reduce or eliminate the overfitting problem. Shrinkage reduces overfitting. On the other hand, if the data set is large (e.g., one has many samples), overfitting is generally not a problem, because the coefficients that are not meaningful will be minimal. Finally, one has a set of coefficients that are highly informative. From the initial training set of correction coefficients, then, one derives a final (modified) set of correction coefficients. This final set of correction coefficient yields an error term (correction term). The error term is then applied to an initial estimate of length (first order estimate length) taken from the backbone contour length in, e.g., a Euclidean distance.

Image Processing

An image may need to be processed before the data from the image can be used in a subject method.

Image processing takes as input a scanning probe microscopy (SPM) e.g., AFM, image of high resolution (e.g., 1024×1024 pixels representing a microscopic area of 1000× 1000 nm) and outputs a set of one-dimensional, eight-connected pixel paths in a transformed image that form the discrete representation of the continuous molecule backbone contours.

Length estimation assigns to these backbones numerical values that purport to measure the true end-to-end length of the molecules.

Automated processing methods employ a pipeline of image processing steps. The steps that are usually included are steps that remove noise, extract foreground objects, iteratively erode each two-dimensional object into a joined one-dimensional line structure (tree), and finally prune each tree's branches from its trunk—the backbone contour to be measured next. The erosion (alternatively called thinning or skeletonizing) algorithms employed include those surveyed in Lam et al. (1992) *IEEE Trans. Patt. Anal. Mach. Intel.* 14:869. Some of the automated methods insert a step after erosion that uses a line-continuity heuristic to decide whether to recover tip pixels that were eliminated during the erosion step. See, e.g., Spisz et al. (1998) *Med. Biol. Eng. Comput.* 36:667; Ficarra et al. (2005) *IEEE Trans. Info. Technol. Biomed.* 9:4:508; Ficarra et al. (2002) *IEEE Intl. Symp. Biomed. Imaging* 17:10:30.0453. One suitable automated method innovates the last, tree-pruning step by transforming it from a strict image processing problem to a graph optimization one, where instead of eliminating branch pixels until the trunk is encountered, the tree is represented as a graph. In this scheme, a node is a pixel at the point of path bifurcation or path termination; an arc is a pixel path whose weight is given by a linear combination of two types of distance, determined by the relative orientations of consecutive pixel pairs: unit distance for horizontal and vertical, $\sqrt{2}$ (square root of 2) for diagonal; the longest path traversal through this graph represents the trunk.

Method for Determining a Nucleic Acid Length

In some embodiments, a subject method is used to determine the length of a nucleic acid, in base pairs. A subject method can be used to measure the total length of a nucleic acid molecule. A subject method can be used to measure the distance between two markers ("identifying features") on a nucleic acid molecule. A subject method can be used to identify a nucleic acid on the basis of a pattern of identifying features (an "identifying features pattern"), by measuring the distance between two or more identifying features.

In some embodiments, the length is measured in nanometers (nm) or micrometers (μm). The length, in nanometers or micrometers, of the nucleic acids can be converted to length in base pairs (bp). The conversion can be carried out manually, e.g., by a human. Alternatively, the conversion can be carried out by a computer program. In general, 0.33 bp is equivalent to about 1 nm; and 30 bp is equivalent to about 10 nm.

In some embodiments, the nucleic acid is immobilized, e.g., in connection with a scanning probe imaging technique, such as AFM. In some embodiments, the immobilized nucleic acid is modified in situ with one or more modifying agents, to generate identifying markers(s) ("identifying features"). In other embodiments, a nucleic acid is modified to generate identifying features before being immobilized. Suitable modifying agents include, e.g., nucleotide sequence-specific modifying agents such as restriction endonucleases; nicking restriction endonucleases; methylation pattern-sensitive modifying agents, e.g., restriction endonucleases that digest DNA that is unmethylated, but that do not digest methylated DNA; enzymes that methylate DNA; a bisulfide (e.g., sodium bisulfite); a hybridizing nucleic acid; a nucleic acid-binding protein; detectable labels; and the like. See, e.g., U.S. Patent Publication No. 2007-0092905.

Restriction Endonuclease Recognition Sites

As one example, the marker (identifying feature) is a restriction enzyme recognition site. For example, in some embodiments, an immobilized nucleic acid is modified by contacting immobilized nucleic acids with one or more restriction endonucleases under conditions such that the immobilized nucleic acids are cleaved in a sequence-specific manner by the restriction endonucleases, and immobilized restriction fragments are generated. In these embodiments, the identifying feature is a restriction endonuclease pattern. The restriction endonuclease pattern is detected using scanning probe microscopy (SPM) (e.g., AFM), where a gap generated by the restriction endonuclease is detected. The AFM tip rasters along the lengths of the immobilized restriction fragments and detects gaps (e.g., restriction endonuclease cleavage sites). The distance between two gaps is a restriction fragment length.

Suitable restriction endonucleases include restriction endonucleases that recognize four-nucleotide sequences; restriction endonucleases that recognize six-nucleotide sequences; restriction endonucleases that recognize eight-nucleotide sequences; and the like. A wide variety of restriction endonucleases are known in the art; any restriction endonuclease can be used. Examples of literature sources of restriction endonucleases and their recognition sequences include: Burrell M. M., ed. (1993). *Enzymes of Molecular Biology*. Humana Press Inc., New York; and Kessler C., et. al. (1985). Recognition sequences of restriction endonucleases and methylases—a review. *Gene* 33: 1-102.

In some embodiments, the immobilized nucleic acid is contacted in situ with one or more restriction endonucleases, under conditions that permit cleavage of the nucleic acid with the restriction endonuclease(s). The restriction endonucleases generate gaps in the immobilized nucleic acid, generating restriction fragments. The length of the restriction fragments is measured as the distance between the gaps. In addition, the location of restriction endonuclease sites can be used to identify a nucleic acid. For example, the pattern of restriction endonuclease sites can be used to identify a nucleic acid.

Nicking Restriction Endonucleases

In some embodiments, the identifying feature is a restriction endonuclease recognition site, where the restriction endonuclease is a nicking restriction endonuclease that cleaves only one strand of a double-stranded nucleic acid, in a sequence-specific manner. In these embodiments, a nucleic acid can be contacted with a nicking restriction endonuclease in solution before being immobilized. Contacting a nucleic acid with a nicking restriction endonuclease, where the nucleic acid comprises a nucleotide sequence recognized by the nicking restriction endonuclease, results in a nucleic acid having a nick site (where "nick site" refers to the site at which a double-stranded DNA molecule has been nicked). The nick site can be labeled in such a manner that it is readily detectable via AFM. For example, a nucleic acid comprising a nick site can be contacted with a polymerase (e.g., a Taq polymerase) or a terminal deoxynucleotide transferase (TdT), where the polymerase incorporates a labelled nucleotide into the nicked nucleic acid, generating a nucleic acid comprising a label at or near the nick site.

For example, as depicted in FIG. 11, a nicked double-stranded cDNA is labeled via terminal transferase with biotin-dUTP, where the biotin-dUTP is incorporated into the nucleic acid at the site of the nick. The biotin-dUTP-containing nucleic acid is then contacted with a biotin-binding protein such as streptavidin. Where two or more such nicks are formed in a nucleic acid, the length between two or more nicks can be measured. The pattern of nicks can be used to identify a nucleic acid.

Nicking restriction endonucleases (sequence-specific nicking restriction endonucleases) are known in the art, and any nicking restriction endonuclease can be used to provide an identifying feature. Nicking restriction endonucleases include, but are not limited to: Nt.BsmAI (recognition sequence: gtctc); Nt.AlwI (recognition sequence: ggatc); Nt.BsmI (recognition sequence: gaatgc); Nt.BsrDI (recognition sequence: gcaatg); Nt.CviPII (recognition sequence: ccd); Nt.Bpu10I (recognition sequence: cctagc); Nt.BbvCI (recognition sequence: cctcagc); Nt.Mva1269I (recognition sequence: gaatgc); Nt.B st9I (recognition sequence:gagtc); Nt.BstNBI (recognition sequence:gagtc); Nt.BtsI (recognition sequence: gcagtg); and Nt.BspQI (recognition sequence: gctcttc).

Methylation

In other embodiments, the length between two methylation sites is measured. For example, in some embodiments, immobilized nucleic acid is contacted with one or more agents that methylate DNA, where the contacting provides for methylation of the DNA. In these embodiments, the identifying feature is a methylation pattern. Detection of the methylation pattern will in many embodiments involve cleaving the methylated DNA with one or more restriction endonucleases that discriminate between methylated and unmethylated DNA. The pattern of gaps generated by the action of the restriction endonucleases is detected as described above for restriction fragments. The pattern of methylation sites can be used to identify a nucleic acid.

Methylating agents include bisulfide agents, many of which are known in the art. Restriction endonucleases that discriminate between methylated and unmethylated DNA are known in the art; and any known endonuclease can be used. As one non-limiting example, MboI does not cleave the sequence $G^mATC$ (where $^mA$ is methylated adenine), while Sau3AI does cleave $G^mATC$. Similarly, HpaII does not cleave $C^mCGG$, while MspI does cleave $C^mCGG$. Other methylation pattern-sensitive restriction endonucleases are known in the art. See, e.g, McClelland et al. (1994) *Nucleic Acids Res.* 22(17):3640-59.

Hybridization with a Nucleic Acid Probe

In some embodiments, the modifying step involves contacting immobilized nucleic acids with one or more nucleic acid probes under conditions that favor or promote hybridization of the nucleic acid probe with the immobilized nucleic acids. In these embodiments, the identifying feature is hybridization with a nucleic acid probe, and detecting the identifying feature involves detecting a height difference between unhybridized immobilized nucleic acid and hybridized immobilized nucleic acid. In some embodiments, the pattern of hybridization of a probe (or multiple probes) to a nucleic acid can be used to identify the nucleic acid.

A hybridizing nucleic acid (a "nucleic acid probe") is a nucleic acid that hybridizes with an immobilized nucleic acid. Suitable nucleic acid probes include DNA; RNA; peptide nucleic acid (PNA); locked nucleic acid (LNA); and the like. PNA is described in numerous publications, including, e.g., Paulasova and Pellestor (2004) *Ann. Genet.* 47:349-358; and "Peptide Nucleic Acids: Protocols and Applications" (2004) $2^{nd}$ Edition, P. E. Nielsen, Ed., Horizon Bioscience. LNA is described in numerous publications, including, e.g., Vester and Wengel (2004) *Biochem.* 43:13233-41; and Petersen and Wengel (2003) *Trends Biotechnol.* 21:74-81.

In some embodiments, a modifying agent is a nucleic acid that hybridizes under stringent hybridization conditions to an immobilized nucleic acid. Nucleic acid probes can be of various lengths, e.g., from about 5 nucleotides to about 100 nucleotides in length, e.g., from about 5 nucleotides to about 10 nucleotides, from about 10 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 50 nucleotides, from about 50 nucleotides to bout 75 nucleotides, or from about 75 nucleotides to about 100 nucleotides in length. Nucleic acid probes can be generated using any known method, e.g., chemical synthesis; cleavage of a nucleic acid with one or more restriction endonucleases to generate fragments, where a fragment may be purified by, e.g., gel electrophoresis; recombinant methods; and the like.

Duplex Formation

In some embodiments, an identifying feature is duplex formation. Duplex formation can take place in the context of secondary structure (e.g., hairpin formation), e.g., secondary structure that may form in an RNA molecule; in the context of nucleic acid hybridization (e.g., hybridization of a probe nucleic acid to a test nucleic acid); or in the context of nucleic acid that is normally double-stranded. A single nucleic acid can have regions that are double stranded and regions that are single stranded. For example, a nucleic acid can have alternating double stranded and single stranded regions. The pattern of double-stranded and single-stranded regions in a nucleic acid can be detected, e.g., by the angle at which the double-stranded and single-stranded regions form relative to one another. The pattern of double-stranded and single-stranded regions can be used to identify a nucleic acid.

Melting Temperature

In some embodiments, an identifying feature is melting temperature, e.g., a pattern of melting temperature. For example, the temperature can be changed (e.g., increased) during scanning probe microscopy (e.g., AFM) imaging of a double-stranded nucleic acid, and regional melting of the nucleic acid can be detected, e.g., by detecting shape changes and/or mechanical properties (e.g., adhesive properties; stiffness) of the nucleic acid. The pattern of melting within a double-stranded nucleic acid can be used to identify the nucleic acid.

Binding with a Nucleic Acid Binding Protein

In some embodiments, the modifying step involves contacting immobilized nucleic acids with one or more proteins that bind DNA, under conditions that favor DNA-protein binding. In these embodiments, the identifying feature is binding of the protein(s) to the immobilized nucleic acid, and detecting the identifying feature involves detecting a height difference between immobilized nucleic acid without bound protein and immobilized nucleic acid with bound protein. DNA-binding proteins include, but are not limited to, histones, transcription factors, DNA polymerases, RNA polymerases, and the like. In addition, the location of protein binding sites can be used to identify a nucleic acid. For example, the pattern of protein binding sites can be used to identify a nucleic acid.

Modification with Detectable Label

In some embodiments, the modifying step involves modifying immobilized nucleic acids with one or more labeling agents. In these embodiments, the identifying feature is labeled immobilized nucleic acid, and detecting the identifying feature involves detecting a height difference between labeled immobilized nucleic acid and unlabeled immobilized nucleic acid.

Suitable labeling agents include fluorochromes, e.g. fluorescein isothiocyanate (FITC), rhodamine, Texas Red, phycoerythrin, allophycocyanin, 6-carboxyfluorescein (6-FAM), 2', 7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA); detectable proteins; biotin; antibodies; engineered nanoparticles of known dimensions; polymer chains of known dimensions; non-fluorescent nucleic acids of any length; and the like. Detectable labels also include peptides (e.g., epitope tags) or polypeptides that can be detected by antibody binding, e.g., by binding of a detectably labeled antibody or by detection of bound antibody.

Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP, which is available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like.

Also suitable for use are quantum dots (e.g., detectably labeled semiconductor nanocrystals, such as fluorescently labeled quantum dots, antibody-conjugated quantum dots, and the like). See, e.g., Dubertret et al. 2002 *Science* 298:759-1762; Chan et al. (1998) *Science* 281:2016-2018; U.S. Pat. No. 6,855,551; Bruchez et al. (1998) Science 281:2013-2016.

Computer Program Product and System

The present invention further provides a computer program product for carrying out a subject method.

Figure 9:
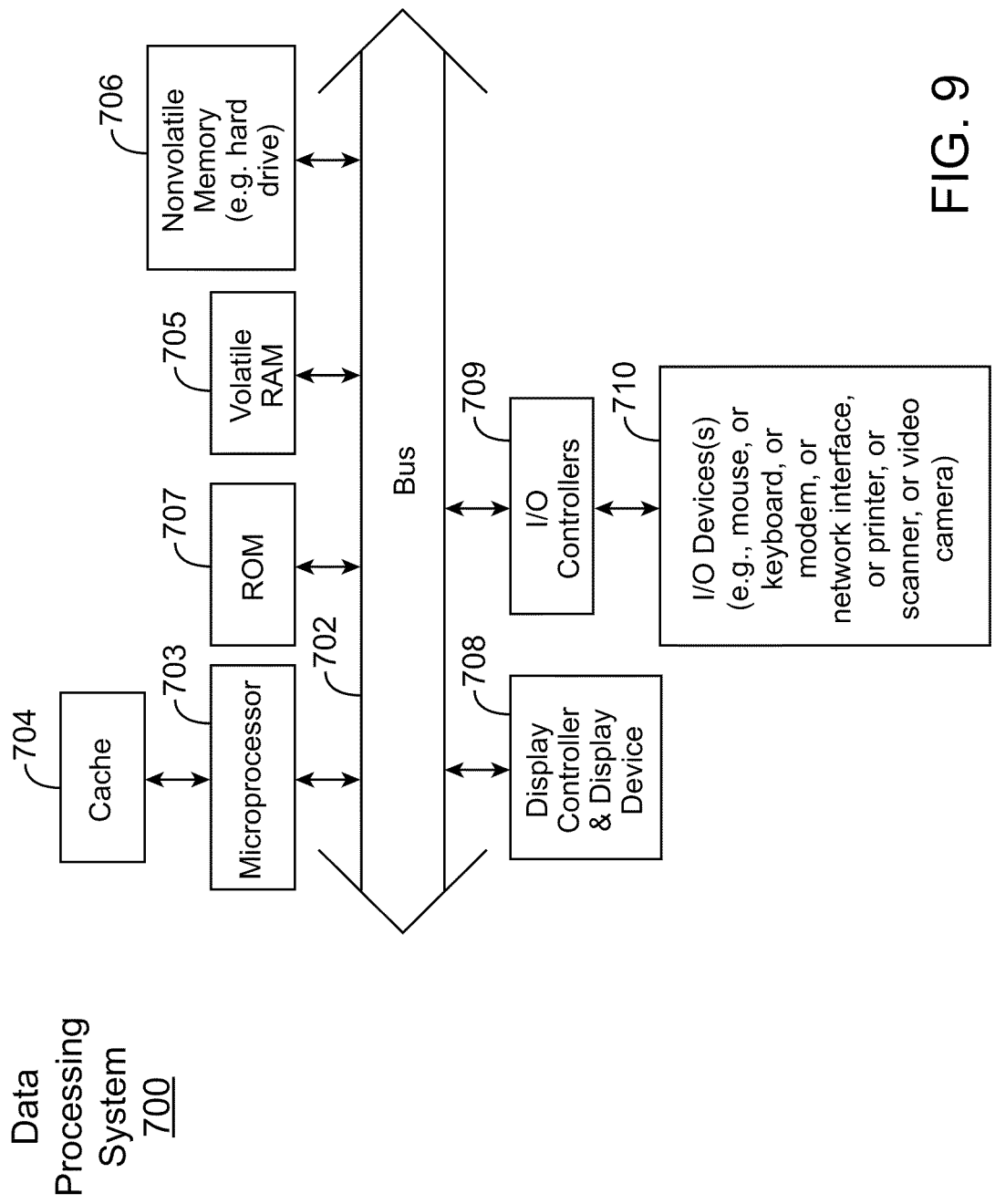
FIG. 9 illustrates an example data processing system in which the present invention may be implemented

FIG. 9 illustrates an example data processing system in which the present invention may be implemented. As shown in FIG. 9, the data processing system 701 includes a system bus 702 which is coupled to a microprocessor 703, a read-only memory (ROM) 707, a volatile random access memory (RAM) 705, and other non-volatile memory 706 such as electronic or magnetic disk storage. The microprocessor 703, which may be a processor designed to execute any instruction set, is coupled to cache memory 704 as shown in the example of FIG. 9. The system bus 702 interconnects these various components together and also interconnects components 703, 707, 705, and 706 to a display controller and display device 708, and to peripheral devices such as input/output (I/O) devices 710, such as keyboards, modems, network interfaces, printers, scanners, video cameras and other devices which are well known in the art. Typically, the I/O devices 710 are coupled to the system bus 702 through input/output controllers 709. The volatile RAM 705 is typically implemented as dynamic RAM (DRAM) which requires power continually in order to refresh or maintain the data in the memory. The non-volatile memory 706 is typically a magnetic hard drive or a magnetic optical drive or an optical drive or a DVD RAM or other type of memory systems which maintain data even after power is removed from the system. While FIG. 9 shows that the non-volatile memory 706 is a local device coupled directly to the rest of the components in the data processing system, it will be appreciated that the present description may utilize a non-volatile memory which is remote from the system, such as a network storage device which may be coupled to the data processing system through a network interface such as a modem or Ethernet interface. The system bus 702 may include one or more buses connected to each other through various bridges, controllers and/or adapters (not shown) as is well known in the art. In one embodiment the I/O controller 709 includes a USB (Universal Serial Bus) adapter for controlling USB peripherals, and/or an IEEE-1394 bus adapter for controlling IEEE-1394 peripherals. Additionally, it will be understood that the various embodiments described herein may be implemented with data processing systems which have more or fewer components than system 700.

Computational Analysis

Figure 10:
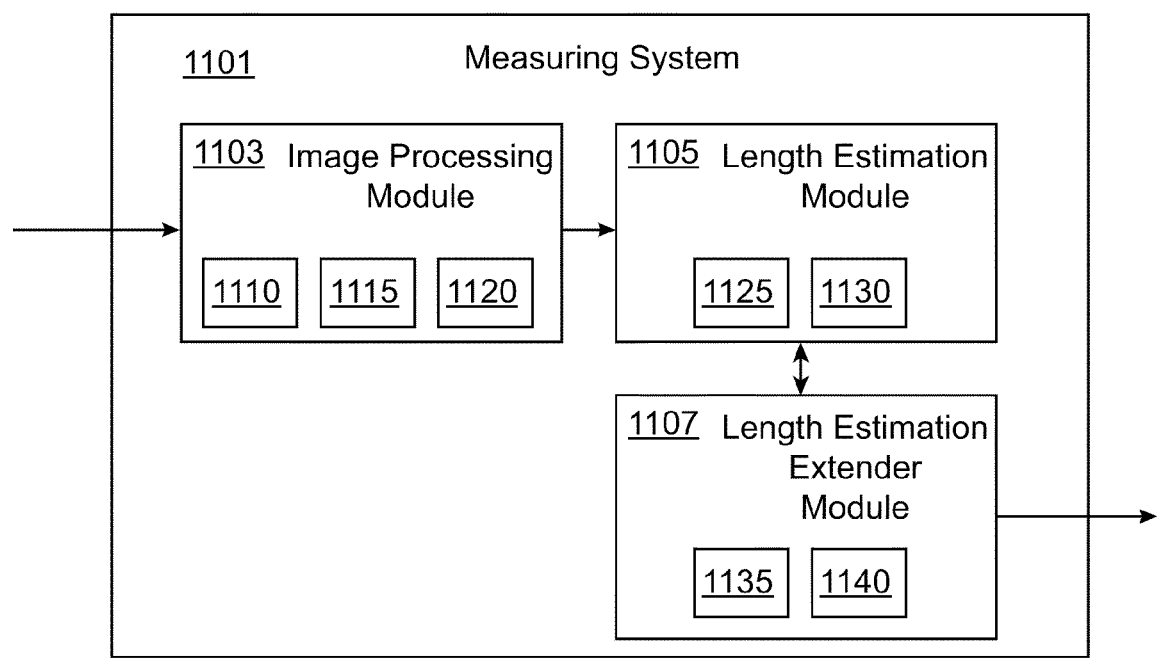
FIG. 10 illustrates an exemplary measuring system.

The present disclosure provides for a measuring system 1101 comprising image processing module 1103, length estimation module 1105, and length estimation extender module 1107, as shown in FIG. 10. The measuring system 1101 and the modules therein may be implemented, for example, in a data processing device or system—e.g., the exemplary computer shown in FIG. 9. It should be appreciated that the measuring system may be part of a larger system and operably coupled to the computer.

Image processing module 1103 executes the image processing pipeline technique to convert an image (e.g., an AFM image) into a molecular backbone image for measurement. Example image processing operations may include, but are not limited to, a filtering operation, an erode operation, and a select operation, as represented by filter module 1110, erode module 1115, and select module 1120, respectively. It should be appreciated that in various embodiments, one or more of these modules may be present in image processing module 1103, and that one or more of these modules may be absent from image processing module 1103. For example, FIG. 1 depicts exemplary operations, including a filtering operation, an erode operation, and a select operation, for the exemplary image processing module. It should be appreciated that all or part of the description of FIG. 1 (as provided in Example 1 and within FIG. 1) may also apply to the above-described image-processing module depicted in FIG. 10.

The length estimation module 1105 receives the resulting data from the processing module 1103, and provides a length estimate. As shown in FIG. 11, the length estimate can comprise an initial estimate and a secondary estimate, as represented by initial estimation module 1125 and secondary estimation module 1130, respectively. For example, the initial estimation module 1125 can provide an initial estimation based on line segments, as described in Example 1, to generate an initial estimate value $L_{LS}$. As another example, the secondary estimation module 1130 can apply a sequence of cubic splines to the length estimation generated by initial estimation module 1125, to generate a secondary estimate value $L_{CS}$. The length estimation module 1105 thus provides a length estimate.

Figure 3:
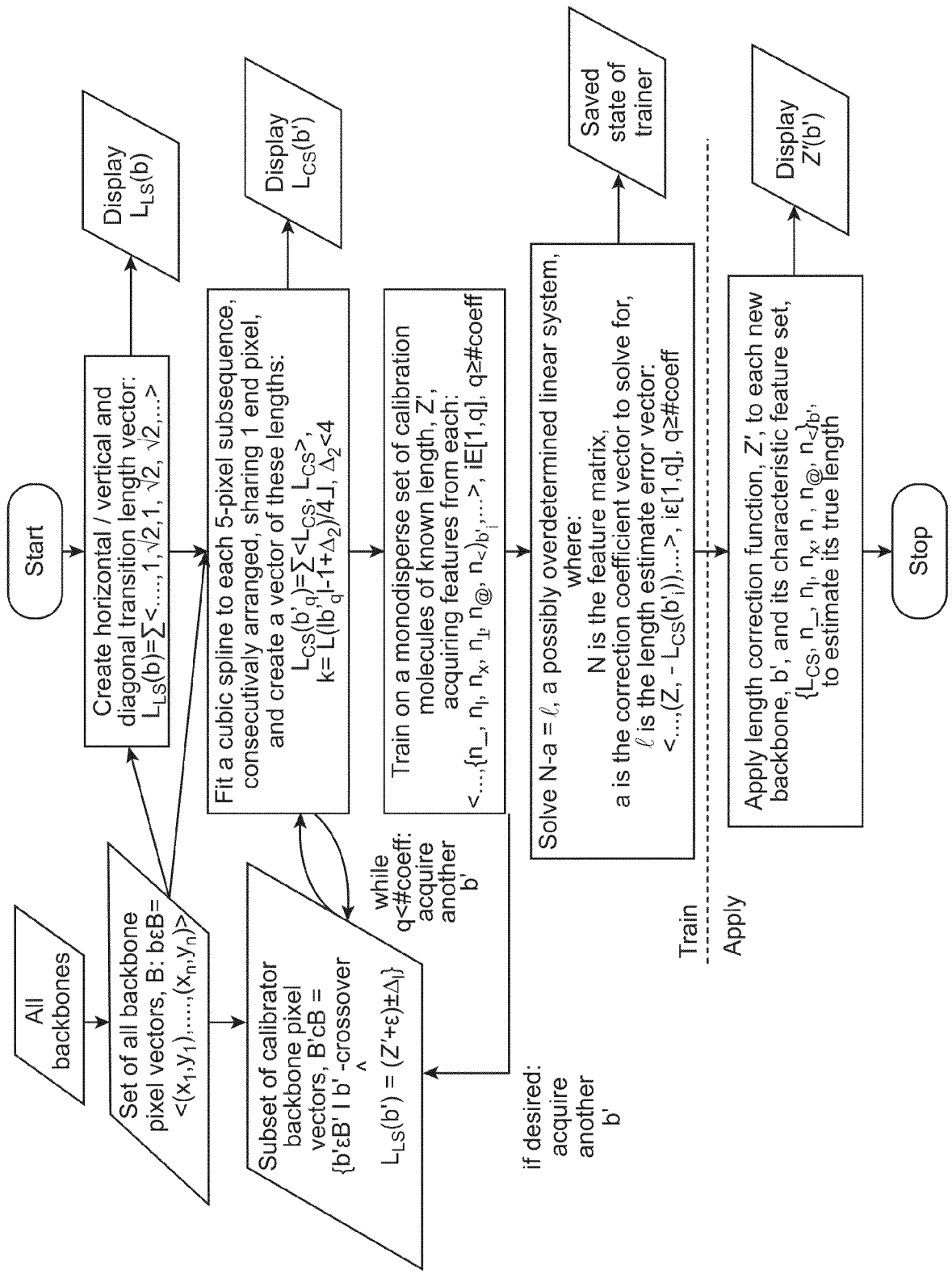
FIG. 3 depicts the AFM Explorer length estimation pipeline.

As shown in FIG. 11, a length extender module may also be included to train on a set of known calibration molecules, to generate a correction term, and to apply the correction term to the length estimate, resulting in a high-accuracy length measurement. The length estimation extender module 1107 includes train module 1135 and apply module 1140, and accordingly executes the function and operation of each, as described herein. Train module 1135 generates a training set of correction coefficients. In some embodiments, train module 1135 further modifies the training set of correction coefficients using a shrinkage method, a weighting method, or both shrinkage and weighting, to generate a modified set of correction coefficients. The training set of correction coefficients or the modified set of correction coefficients is used to generate a correction term ("error term"). Apply module 1140 applies the correction term to the length estimate, thereby generating a highly accurate length measurement. For example, FIG. 3 depicts exemplary operations for a train module and an apply module. It should be appreciated that all or part of the description of FIG. 3 (as provided in Example 1 and within FIG. 3) may also apply to the above-described length estimation module and length estimation extender module depicted in FIG. 10.

In some embodiments, the high accuracy measurement may be used to identify and/or generate identifying feature patterns for a measured macromolecule, or portion thereof. The identifying feature patterns may be used in a variety of ways, depending on the specific application. For example, the identifying feature patterns may be compared to known identifying feature patterns for known macromolecules or portions thereof. These known identifying feature patterns are also referred to herein as "reference identifying feature patterns". The comparison may be used, for example, to identify the measured macromolecule, or portion thereof, and/or any other analysis purposes. For instance, an identifying feature pattern for a measured nucleic acid may be identified and compared to a library of reference identifying feature patterns for known nucleic acids. In some embodiments, where the macromolecule is a nucleic acid, the nucleic acid is present in the sample in an abundance of from about 1 nucleic acid molecule per $10^2$ nucleic acid molecules to about 1 nucleic acid molecule per $10^6$ nucleic acid molecules.

As another example, identifying feature patterns for each of a plurality of population of nucleic acids (e.g., mRNAs of cDNA copies thereof) in a cell may be used to generate a gene expression profile of the cell. The identifying feature patterns and/or gene expression profile of the cell may then be compared with reference identifying feature patterns and/or known gene expression profiles (also referred to herein as "reference gene expression profiles") for identification or analysis purposes. Any variety of types of cells may be used for a variety of reasons depending on the specific application. In some instances, the cell may be a mammalian cell. In some instances, a diseased cell may be used. A profile from a diseased cell may be, for example, compared with a profile from a normal cell of the same cell type as the diseased cell. As another example, the profile of a diseased cell may be compared to a library of profiles stored in a reference database for identification.

In some embodiments, reference identifying feature patterns and/or reference gene expression profiles may be stored within a reference database within, or operably coupled, to the computer and/or measuring system. It should be appreciated that the reference database may be implemented as any variety of memory or storage devices located locally or remotely to the computer—e.g., CD-ROM, RAM, Flash, hard drives, etc. In some instances, the reference database may be located remotely and downloaded to the computer via the internet.

In some embodiments, the measurement may be further displayed on a display device operably coupled to the processor, computing device, computer system, etc. In some embodiments, the measurement may be further stored in a storage arrangement in at least one of a user-accessible format or a user-readable format. It should be appreciated that such storage arrangement may comprise, for example, any of the storage and memory devices, and implementations, discussed herein.

It will be apparent from this description that aspects of the measuring system and its modules may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

In addition, the processor(s) may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices. In alternative embodiments, special-purpose hardware such as logic circuits or other hardwired circuitry may be used in combination with software instructions to implement the techniques described herein.

The present disclosure further provides a computer program stored on a computer-readable storage medium, which program, when read by a computer, executes one or more of the following: a) determination of a test metric of an object; b) generation of a training set of images using a known metric of an object; c) application of a correction factor or set of correction factors to a known metric, generating an empirically learned correction term (e.g., a weighted factor or set of weighted factors); d) application of an empirically learned correction term (e.g., a weighted factor or set of weighted factors) to a test metric, generating a high-accuracy metric of an object.

In some embodiments, a subject computer program will have stored therein a subject algorithm, which algorithm weights the correction factor(s). In some embodiments, a subject computer program will have stored therein a subject algorithm, which algorithm weights the correction factor(s) and applies the weighted correction factor(s) to a test metric.

In some embodiments, the present disclosure provides a computer system for determining a high-accuracy metric of an object. The computer system generally comprises: a) a central computing environment; b) an input device operatively connected to the computing environment, to receive test metric information; c) an algorithm (or computer program product) executed by the central computing environment (e.g., a processor), wherein the algorithm is executed based on the test metric received by the input device, such that the computer program product executes one or more of: i) generation of a training set of images using a known metric of an object; ii) application of a correction factor or set of correction factors to a known metric, generating an empirically learned correction term (e.g., a weighted factor or set of weighted factors); iii) application of an empirically learned correction term (e.g., a weighted factor or set of weighted factors) to a test metric, generating a high-accuracy metric of the object.

The present disclosure further provides a system for providing a high-accuracy metric of an object, where a subject system comprises: a) a device for generating a test metric; and b) a subject computer system. The device for generating a test metric can be operably linked to the computer system, where a test metric generated by the device is sent directly to an input device. A non-limiting example of a device for generating a test metric is an atomic force microscope. However, a device for generating a test metric can be any device that measures a feature of an object.

The data input device (also referred to as an operator input device) may be, e.g., a keyboard, a mouse, and the like. The processor has access to a memory, which may be any suitable device in which the processor can store and retrieve data, such as magnetic, optical, or solid state storage devices (including magnetic or optical disks or tape or RAM, or any other suitable device). The processor can include a general purpose digital microprocessor (such as is typically used in a programmable computer) suitably programmed to execute an algorithm as described above, or any hardware or software combination which will perform the required functions.

In some embodiments, a subject computer system further includes a device for storing the input data (e.g., test metric). In some embodiments, a subject system further includes a library of reference data (e.g., metric(s) used in the training set to generate the weighted correction factors) stored in a suitable storage medium. In some embodiments, a subject computer system further includes a device for storing the output data (e.g., the high-accuracy metric data).

The computer program may be recorded on hardware or non-transitory tangible media—e.g., that can be read and accessed directly or indirectly by a computer and/or processing arrangement. For example, the computer program may be stored on a computer readable media including, but not limited to, for example: magnetic tape; optical storage such as compact disc-read only memory (CD-ROM) and digital versatile disk (DVD); electrical storage media such as random access memory (RAM), read-only memory (ROM), Flash memory; hybrids of these categories such as magnetic/optical storage media; etc. One of skill in the art can readily appreciate how any of the presently known computer readable media can be used to create a manufacture that includes a recording of the present programming/algorithms for carrying out the above-described method. In certain embodiments, the programming is further characterized in that it provides a user interface, where the user interface presents to a user the option of selecting among one or more different, including multiple different, criteria. The instructions may include installation or setup directions. The instructions may include directions for use of the invention.

In addition, a subject system will typically include instructions for using the system to carry out a subject method. The instructions of the above-described system are generally recorded on a suitable recording medium. For example, the instructions may be printed on a substrate, such as paper or plastic, etc. As such, the instructions may be present in the system as a package insert, or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the system, but means for obtaining the instructions from a remote source, e.g. via the Internet, are provided. An example of this embodiment is a system that includes a web address where the instructions can be viewed and/or from which the instructions can be downloaded. Conversely, means may be provided for obtaining the subject programming from a remote source, such as by providing a web address. Still further, the system may be one in which both the instructions and software are obtained or downloaded from a remote source, as in the Internet or World Wide Web. Some form of access security or identification protocol may be used to limit access only to those entitled to use the subject invention. As with the instructions, the means for obtaining the instructions and/or programming is generally recorded on a suitable recording medium.

The foregoing description has been directed to specific embodiments of this invention. It will be apparent to persons of skill in the art; however, that other variations and modifications may be made to the described embodiments, while maintaining some or all of their advantages. For example, it will be apparent from this description that aspects of the present disclosure may be embodied, at least in part, in software, hardware, firmware, or in combination thereof. The techniques described herein may be carried out in a computer system or other data processing system in response to its processor, such as a microprocessor, executing sequences of instructions contained in a memory, such as a ROM, volatile RAM, non-volatile memory, cache memory, or other remote storage device memory. In various embodiments, hardwired circuitry may be used in combination with software instructions to implement this present description. Thus, the techniques are not limited to any specific combination of hardware circuitry and/or software, or to any particular source for the instructions executed by a data processing system Additionally, the apparatuses described herein may be specially constructed for the required purposes, or they may comprise a general purpose computer selectively activated or configured by a computer program stored in a memory of the computer. Such a computer program may be stored in a computer-readable medium. A computer-readable medium can be used to store software instructions, which when executed by a data processing system, causes the system to perform the various methods of this description. A computer-readable medium may include any mechanism that provides information in a form accessible by a machine (e.g., a computer, network device, personal digital assistant, or any device with a set of one or more processors). For example, a computer-readable medium may include any type of disk including floppy disks, hard drive disks (HDDs), solid-state devices (SSDs), optical disks, CD-ROMs, and magnetic-optical disks, ROMs, RAMs, EPROMs, EEPROMs, other flash memory, magnetic or optical cards, or any type of media suitable for storing instructions in an electronic format.

Throughout the foregoing description, for the purposes of explanation, numerous specific details were set forth in order to provide a thorough understanding of the invention. It will be apparent, however, to one skilled in the art that the invention may be practiced without some of these specific details. In addition, embodiments of the invention may include various operations as set forth above, or fewer operations or more operations, or operations in an order which is different from the order described herein. Accordingly, the scope and spirit of the invention should be judged in terms of the claims which follow as well as the legal equivalents thereof.

Utility

The subject methods find use in a variety of research and diagnostic applications. A nucleic acid (or other macromolecule), or a portion of a nucleic acid, can be measured, where the measurement can provide for detection of a particular nucleic acid.

As one non-limiting example, a subject method can be used to measure the length (and hence the molecular weight) of nucleic acids present in or obtained from a single cell. Of particular interest in some embodiments is the identification or detection of a nucleic acid in a sample, where the nucleic acid is identified by detecting a pattern of identifying features in the nucleic acid.

A single cell contains $10^5$-$10^6$ mRNA molecules; low abundance mRNA species may be present in only a few copies per cell. A subject method allows one to measure, with high accuracy, the length of nucleic acids, including a low-abundance mRNA, in a single cell.

A subject method allows discrimination between two nucleic acids differing in length by less than about 20 nucleotides (nt), e.g., a subject method allows discrimination between two nucleic acids differing in length by from about 1 nt to about 5 nt, from about 5 nt to about 10 nt, from about 10 nt to about 15 nt, or from about 15 nt to about 20 nt. Such discrimination allows one to distinguish between, for example, alternatively spliced mRNAs (or cDNA copies thereof).

As noted above, a subject method provides for identification of a nucleic acid by detecting a pattern of identifying features in a nucleic acid. For example, the distance between multiple (two, three, four, five, six, seven, eight, nine, ten, or more) identifying features in a test nucleic acid is measured using a subject method, where such identifying features include, but are not limited to, restriction endonuclease recognition sites; methylation sites; nucleic acid hybridization sites; alternatively spliced mRNAs; patterns of duplex and single-stranded regions; protein binding sites; melting temperature; and a site of binding of any binding element (e.g., a nucleic acid probe; a nanoparticle; a quantum dot; a protein; a dye); and the like. The result of measuring the distance between multiple identifying features is a pattern, e.g., an identification pattern. A match between the identification pattern of a test nucleic acid and a known identification pattern of a known nucleic acid provides an indication of the identity of the test nucleic acid, i.e., indicates that the test nucleic acid and the known nucleic acid are substantially the same.

As an example of a method of identifying a nucleic acid by an identifying feature pattern, one can determine the distance between identifying features a, b, c, d, e, and f, where the length between identifying features a and b is $l_1$, where the length between identifying features b and c is $l_2$, where the length between identifying features c and d is $l_3$, where the length between identifying features d and e is $l_4$, and where the length between identifying features e and f is $l_5$. As an example, $l_1$, $l_2$, $l_3$, and $l_4$, of a test nucleic acid, are 125 nt, 75 nt, 323 nt, and 56 nt nt, respectively, as measured using a subject method. The test nucleic acid thus has an identifying feature pattern of 125-75-323-56. This "test" identifying feature pattern can be compared to a reference database of identifying feature patterns. Where there is a match between the test identifying feature pattern and the reference identifying feature pattern, such would indicate that the test nucleic acid is substantially the same as a reference nucleic acid having the reference identifying feature pattern.

Gene Expression Profiling Applications

A subject method can be used in gene profiling applications. A subject gene profiling method can be used in various research applications. For example, a subject method can be used to generate a profile of nucleic acids in a single cell. As an example, a subject method can be used to generate a profile of mRNA transcripts (or cDNA copies of the mRNA) from a single cell, to obtain a "transcription profile." A profile of mRNA (or cDNA copies of same) can be obtained from a single cell to provide a transcription profile of the cell, e.g., a profile of the lengths of mRNA transcripts present in the cell.

In some embodiments, a subject method for generating a gene expression profile of a single cell comprises: a) preparing a scanning probe microscopy image of a population of complementary DNAs (cDNAs) synthesized using mRNA obtained from the single cell; b) applying a subject method for obtaining a high-accuracy length of a nucleic acid to the nucleic acids in the image, wherein an identifying feature pattern for each of a plurality of the population of nucleic acids in the cell is produced, thereby generating a gene expression profile of the cell.

In some embodiments, a subject method for generating a gene expression profile of a single cell comprises: applying a subject method for obtaining a high-accuracy length of a nucleic acid to each of a plurality of the population of nucleic acids in a scanning probe microscopy image of a population of complementary DNAs (cDNAs) synthesized using mRNA obtained from the single cell, wherein an identifying feature pattern for each of a plurality of the population of nucleic acids in the cell is produced, thereby generating a gene expression profile of the cell.

In some embodiments, the cell is a eukaryotic cell, e.g., a mammalian cell. In some embodiments, the cell is a diseased cell. In some embodiments, the scanning probe microscopy image is an AFM image, wherein the AFM probe is contacted with the nucleic acid. In some embodiments, the nucleic acid-contacting end of the AFM probe is functionalized with an antibody, a hydrophilic group, a hydrophobic group, a group comprising an electrostatic charge, a probe nucleic acid that hybridizes to the nucleic acid being measured, a protein, a dye, or a magnetic material. In some embodiments, the method further comprises comparing at least one of the identifying feature patterns with a reference identifying feature pattern. In some embodiments, the method further comprises comparing two or more profiles with one another. In some embodiments, the method comprises comparing a first profile from a diseased cell with a second profile from a normal cell of the same cell type as the diseased cell.

A subject method can in some embodiments allow discrimination between alternatively spliced mRNAs, even where the alternatively spliced mRNAs differ in length by fewer than 10 nucleotides.

A subject method can be used to profile nucleic acids in a cell affected by an internal or an external stimulus. A comparison of the profile of nucleic acids in a cell affected by an internal or an external stimulus can be compared too the profile of nucleic acids in a control cell, e.g., a cell not affected by the internal or external stimulus.

External and internal signals (stimuli) include, but are not limited to, infection of a cell by a microorganism, including, but not limited to, a bacterium (e.g., *Mycobacterium* spp., *Shigella, Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Ban virus, and the like; viruses that infect plant cells; etc.); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; a change in phospholipid structure; light; dark; caloric restriction; caloric intake; mitogens, including, but not limited to, lipopolysaccharide (LPS), pokeweed mitogen; stress; antigens; sleep pattern (e.g., sleep deprivation, alteration in sleep pattern, and the like); an apoptosis-inducing signal; electrical charge (e.g., a voltage signal); ion concentration of the medium in which a cell is maintained, or an internal ion concentration, exemplary ions including sodium ions, potassium ions, chloride ions, calcium ions, and the like; presence or absence of a nutrient; metal ions; a transcription factor; a tumor suppressor; cell-cell contact; adhesion to a surface; peptide aptamers; RNA aptamers; intrabodies; and the like.

A subject method can be used to obtain a transcription profile of a single cell as a function of a particular physiological state. For example, a first transcription profile can be obtained in a cell when the cell is in a first physiological state; and a second transcription profile can be obtained in a cell when the cell is in a second physiological state. For example, the first physiological state could be the absence of disease or absence of a condition; and the second physiological state could be a disease state or a particular condition. Thus, for example, a transcription profile can be used to detect the presence of a disease state or a condition. Disease states and other conditions that may be detected include, but are not limited to, cancer, diabetes, obesity, cardiac disorders, liver disorders, skeletal muscle disorders, brain disorders, and the like.

A transcription profile can be taken over time, e.g., to assess the effect of an internal or external stimulus on a cell over time; to assess the effect of an experimental drug on a cell over time; and the like. A first transcription profile can be taken at a first time; and a second transcription profile can be taken at a second time. The first and second transcription profiles can be compared to determine the effect of an agent, drug, stimulus, etc., over time.

A gene expression profile obtained using a subject method can be compared to a reference gene expression profile, or to a database of gene expression profiles.

Detection Applications

A subject method can be a detection method, suitable for use in various research and diagnostic applications, e.g., where detection of a nucleic acid in a single cell is desired or required.

In some embodiments, a nucleic acid is identified or detected by: a) generating, with a computer, an empirically learned correction term; b) applying, with the computer, the empirically learned correction term to an estimated measurement of the distances between two or more identifying features of a plurality of a population of nucleic acids present in a scanning probe microscopy image, thereby generating a high-accuracy measurement of the distance, thereby generating a test identifying feature pattern for each of the plurality of the population of nucleic acids; and c) comparing a test identifying feature pattern to a reference identifying feature pattern of a known nucleic acid, wherein identity between the test identifying feature pattern and the reference identifying feature pattern provides for identification or detection of the nucleic acid in the sample.

In some embodiments, a nucleic acid is identified or detected by: a) applying a method as described above for generating a high-accuracy length of a nucleic acid to a plurality of a population of nucleic acids present in a scanning probe microscopy image, thereby generating a high-accuracy measurement of the distance, thereby generating a test identifying feature pattern for each of the plurality of the population of nucleic acids; and b) comparing a test identifying feature pattern to a reference identifying feature pattern of a known nucleic acid, wherein identity between the test identifying feature pattern and the reference identifying feature pattern provides for identification or detection of the nucleic acid in the sample.

In some embodiments, a subject method of identifying or detecting a nucleic acid in a sample comprises: a) preparing a scanning probe microscopy image of a population of complementary DNAs (cDNAs) synthesized using mRNA obtained from the sample; and b) applying a method as described above for generating a high-accuracy length of a nucleic acid to the nucleic acids in the image, wherein a high-accuracy test identifying feature pattern for each of a plurality of the population of nucleic acids in the cell is produced; and c) comparing a test identifying feature pattern to a reference identifying feature pattern of a known nucleic acid, wherein identity between the test identifying feature pattern and the reference identifying feature pattern provides for identification or detection of the nucleic acid in the sample.

In any of the above embodiments, the population of nucleic acids can be obtained from a single cell, e.g., a eukaryotic cell, e.g., a mammalian cell. In any of the above embodiments, the image is an AFM image.

A subject method can in some embodiments allow discrimination between alternatively spliced mRNAs, even where the alternatively spliced mRNAs differ in length by fewer than 10 nucleotides.

Diagnostic applications of a subject detection include, e.g., detection of a nucleic acid in a diseased cell, e.g., detection of a nucleic acid that is diagnostic of a diseased cell. For example, diagnostic applications include, e.g., detection of a nucleic acid in a cancerous cell (e.g., detection of a nucleic acid that is diagnostic for a cancer cell); detection of a nucleic acid in a pre-cancerous cell (e.g., detection of a nucleic acid that is diagnostic for a pre-cancer cell); detection of a nucleic acid in a virus-infected cell (e.g., detection of a nucleic acid that is diagnostic for a virus-infected cell). Thus, a subject method can be used in a clinical assay.

A "nucleic acid that is diagnostic" for a diseased cell (e.g., a cancer cell, a precancerous cell, a virus-infected cell, etc.) can include a full-length nucleic acid, or a nucleic acid that is between two markers. For example, a nucleic acid that is diagnostic for a particular physiological state can be identified as a length of nucleic acid that is between two restriction endonuclease recognition sites.

A subject method can be used to detect the presence of a disease state or a condition. Disease states and other conditions that may be detected include, but are not limited to, cancer, diabetes, obesity, cardiac disorders, liver disorders, skeletal muscle disorders, brain disorders, virus infection, microbial infection, genetic disorders, and the like.

A subject detection method can be used to detect a rare cell in a population of cells. For example, a subject detection method can be used to detect a stem cell (e.g., an adult stem cell). As another example, a subject detection method can be used to detect a diseased cell (e.g., a cancerous cell, a pre-cancerous cell, a virus-infected cell, etc.) that is present at a very low level in an individual.

A subject detection method can be used in forensics, e.g., where tissue is in limited supply, such that a nucleic acid present in or obtained from one or a few cells can be detected. Forensic applications include, e.g., identification of an individual (e.g., identification of a deceased individual; identification of a perpetrator of a crime; etc.).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Image Analysis of Single Molecule Transcription Profiles with AFM

The system described below provides for high-accuracy measurement of the length of nucleic acids. First, each backbone pixel path was fit with a sequence of cubic splines, one for each five-pixel subpath, where the last pixel of a given subpath is the first pixel of the next (i.e. all subpaths share one extremity pixel). A tailing subpath, $\tau$, having p<5 pixels was handled by fitting a cubic spline to the subpath formed by prepending to $\tau$ the prior 5–p pixels, then counting the spline's length from its closest approach to the first and last pixels in $\tau$. The resulting summed length of the cubic splines gives the initial backbone length estimate, $L_{CS}$.

The $L_{CS}$ was corrected by a linear combination of various features, such as: number of horizontal pixel pairs, number of vertical pixel pairs, number of diagonal pixel pairs, number of corner pixel triplets, mean backbone intensity value (height in an AFM image analysis setting), standard deviation of backbone intensity value, mean backbone thickness measured at each pixel, and standard deviation of backbone thickness. The true length, $\mathcal{L}$, is thus modeled as $L_{CS}$ plus a linear combination of the feature terms plus an error term, $\varepsilon$, where the feature term coefficients derive from an overdetermined system of linear equations obtained from a set of calibrating molecules of known length. It was assumed $\varepsilon \sim N(0, \sigma^2)$ represents a Gaussian noise, thus satisfying the Gauss-Markov condition.

The system described below implements a meta-approach to the problem of feature-based length estimation. Any number of image-based features may be incorporated into the simple linear model in an easily extensible way, giving rise to backbone length estimates whose error is not necessarily constrained by geometric lower bounds in terms of, for example, pixel density (see, e.g., Dorst and Smeulders (1987) *Comp. Vis. Graph. Image Proc.* 40:311; Dorst and Smeulders, In *Vision Geometry, series Contemporary Mathematics*, pages 45-62, American Mathematical Society, 1991; Smeulders et al., In *SPIE Proceedings Series*, volume 3168 (1997)) or multigrid convergence (see, e.g., Klette et al. "On the length estimation of digital curves" Technical report, University of Auckland, May 1999, CITR-TR-45; and Coeurjolly and Klette (2004) *IEEE Trans. Patt. Anal. Mach. Intel.* 25:2:252-258). In this way, our approach subsumes those length estimation formulations comprised in small, fixed sets of backbone chain code parameters cited above. (Reed et al. "Single molecule transcription profiling with AFM.", Nanotechnology, 18:4, 2007).

Each image-based feature provides limited predictive power for backbone contour length. But integrated into a properly chosen model, with each feature contributing according to its demonstrated informativeness during training, in principle, the collective result should be superior to any rendered by strict subsets, provided there is no overfitting. Moreover, outside of computational complexity considerations, there should be no bound on the number of features one applies to the problem.

Methods

Cirrone (Automatic recognition and analysis of DNA molecules by AFM image processing; Master's thesis, Università degli Studi di Catania Facoltá di Ingengneiria, 2007) implemented an application called AFM Explorer, using the wxWidgets and OpenCV libraries. (See, e.g., http://www- .wxwidgets.org/ and http://opencvlibrary.sourceforge.net/). It provides a graphical user interface (GUI) that allows the user to adjust image processing parameters (e.g. select from a set of intensity value thresholding methods and values), adjust the $$\frac{nm}{pixel}$$

(nm/pixel) image density factor, process an AFM image, and save the image at different steps of processing. Loading an AFM image places it in central view. Once the application runs the image through the image processing pipeline, it displays in separate tabbed views the skeletonized molecules and the final backbone contours, and in a separate area it lists the computed backbone contour lengths. The user can click on list entries to highlight the associated molecules in each image view, or vice-versa, allowing the user to establish a clear correspondence between visual and numerical results.

AFM Explorer Image Processing Pipeline

AFM Explorer uses the image processing pipeline schematically presented in FIG. 1. The steps are outlined below (refer to Cirrone, 2007, supra for full algorithmic detail).

FIG. 1: AFM Explorer image processing pipeline. An AFM image undergoes three phases of processing: (I) filter the noise using adaptive, local thresholding, yielding a set of two-dimensional binary image objects, (II) erode these into a set of one-dimensional binary image objects, and (III) select the longest path through each graph representation of the 8-connected component—the final backbone image object.

The pipeline has three phases:

1) Filter

Figure 2A:
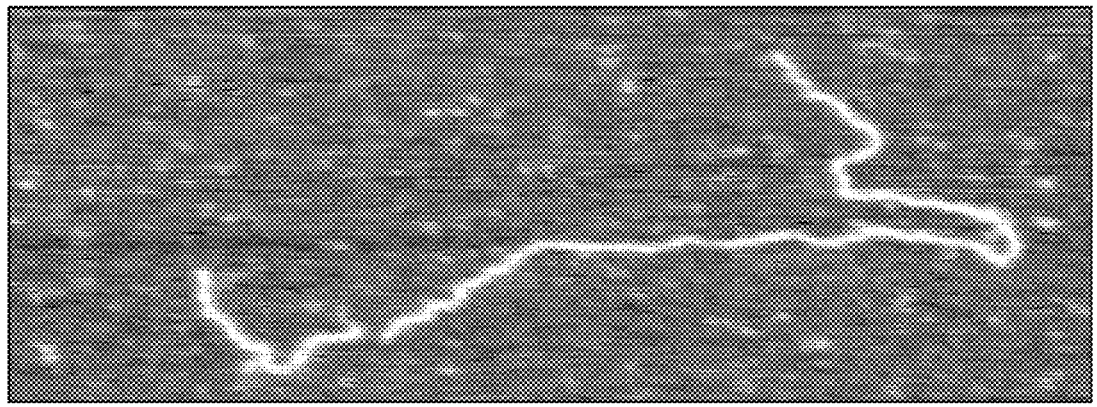
FIGS. 2A-D depict results of the AFM Explore image processing pipeline.

This was implemented as five calls to the OpenCV library. It was begun with a 24-bit RGB image, presumably generated by the AFM apparatus image capture software. (FIG. 2a). It was first converted into an 8-bit grayscale image (cvCvtColor), and then intensity level histogram equalization (cvEqualizeHist) was performed, to increase the local contrast in the image. The image was then smoothed by setting the intensity level of a given pixel to the median intensity level of a 5×5 pixel window about it (cvSmooth). To create a binary image from the smoothed grayscale one, pixels that have an intensity level below an empirically derived static threshold (cvThreshold) were suppressed. In a second pass, a given pixel was adaptively promote to the maximum intensity level if it was brighter than the mean intensity level of a 31×31 pixel window about it; otherwise it was suppressed (cvAdaptiveThreshold).

2) Erode

To obtain a one-dimensional representation of the molecular backbone contours, the erosion algorithm given in Beffert and Shinghal ((1989) *Intl. J. Patt. Reco. Art. Intell.* 3:2:207-216) and Feigin and Ben-Yosef ((1983) In *SPIE Proceedings Series V: Applications of digital Image Processing*, vol. 397, page 108) was employed, which algorithm applies a set of eight 3×3 pixel kernels as structuring elements to iteratively erode the binary regions of 8-connected pixels, halting when there is no change in the images of present and prior iterations. This process results in a set of 8-connected component edge pixels having unit thickness. (FIG. 2b).

3) Select

The image was then a collection of 8-connected component edge pixels. Each component was recursively traversed; distinct branches were labeled, and were according to Euclidean distance from one pixel to the next: {N, S, E, W}=1, {NW, NE, SW, SE}=√2. This traversal resulted in a collection of weighted edge tree graphs. Finally, identified the longest path through each edge tree graph, amounting to pruning branches from the trunk. The longest path represents the molecular backbone contour. Since a simplified algorithm from the one given in Cirrone 2007, supra was implemented, it was defined in Algorithms 1 and 2 (below). The algorithm was two consecutive breadth-first traversals across the 8-connected pixel graph. First, initiated from any extremity (deg=1) pixel, $e_1$, a set of end-to-end pixel paths (with their associated computed lengths), $\mathcal{P}_{e1}$, is constructed through a breadth-first traversal, branching at pixels having more than one unseen neighbor. Second, taking the terminal pixel, $e_2$, of the longest path from $\mathcal{P}_{e1}$, another breadth-first traversal is initiated from $e_2$, constructing its respective set of end-to-end pixel paths, $\mathcal{P}_{ee}$, in the same fashion. Upon completion, the longest path in $\mathcal{P}_{e1} \cup \mathcal{P}_{e2}$ is the longest path in the whole 8-connected pixel graph. (FIG. 2c).

Figure 2B:
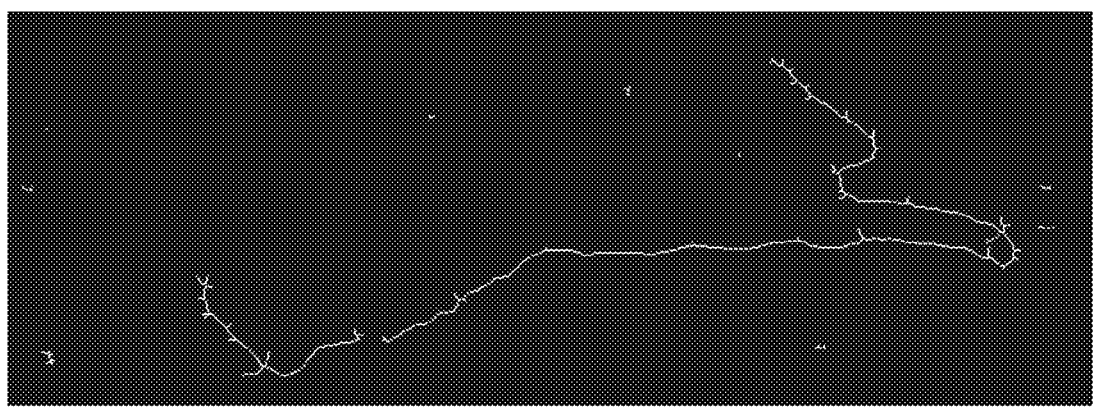
Figure 2C:
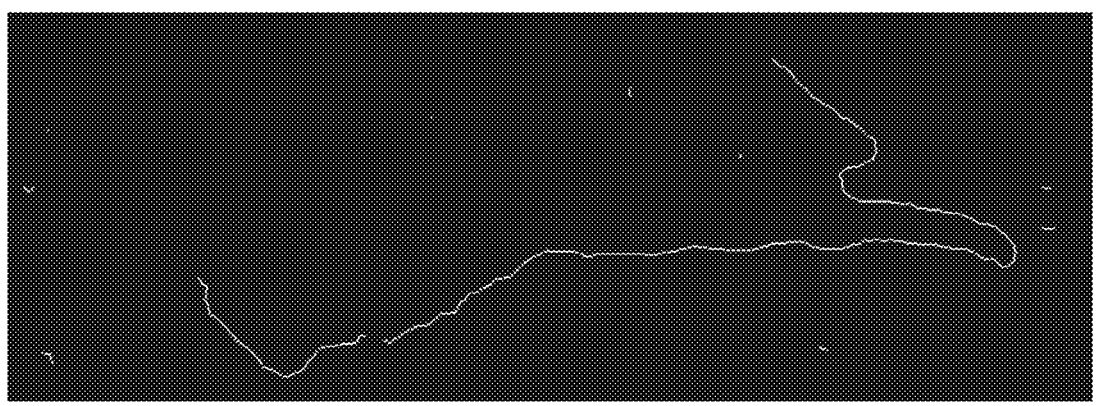
Figure 2D:
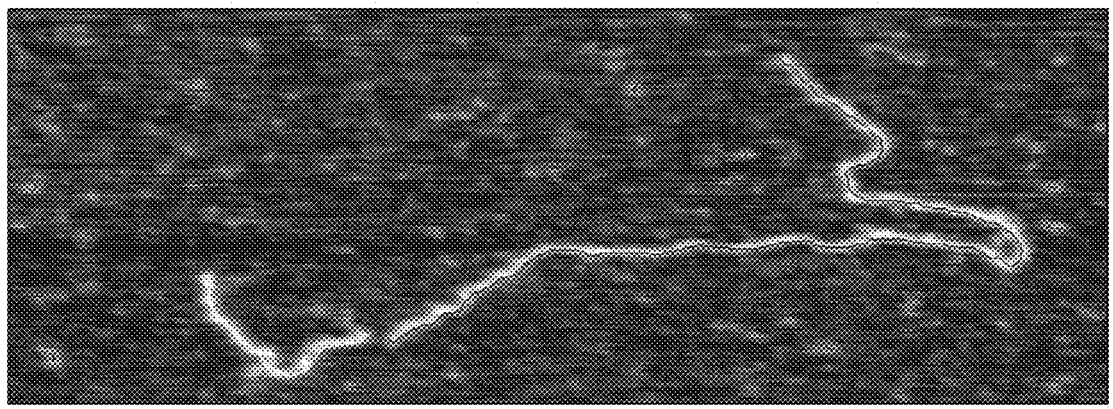

FIGS. 2A-D are results of the AFM Explorer image processing pipeline. FIG. 2A depicts the original 24-bit RGB AFM image. FIG. 2B depicts the image after filtering an iterative erosion. FIG. 2C depicts the image after graph translation and backbone selection. FIG. 2D depicts a backbone (white) with other backbones (black) in the original image.

---

Algorithm 1 Find-Backbones: T → B

Let T be a set of 8-connected pixels forming an n-ary tree (i.e. an image object resulting from an iterative erosion algorithm).

$$\text{Let deg: } t \in T \to N \cap [1, 8] \equiv \sum_{\substack{dx \in \{-1,0,1\}, \\ dy \in \{-1,0,1\}, \\ dx \neq 0 \vee dy \neq 0}} \begin{cases} 1, & \text{if } (t_x + dx, t_y + dy) \in T; \\ 0, & \text{otherwise.} \end{cases}$$

be the degree function that sums the number of pixels in T that are 8-connected with a given pixel in T.
Let $\epsilon = \{e | e \in T, \deg(e) = 1\}$ be the set of extremity pixels in T.
Let adj: $t_a, t_b \in T \to \{true, false\} \equiv |t_{a_x} - t_{b_x}| < 2 \wedge |t_{a_y} - t_{b_y}| < 2$ be the adjacency function that logically determines if two pixels in T are 8-connected with each other.
Let $P = \{p | p = (p_1, p_2, \ldots p_n, p_i \in T, 1 \le i \le n, p_j \in \epsilon, j \in \{1, n\}, p_k \notin \epsilon, 1 < k < n, \text{adj}(p_a, p_b), 1 \le a < n,$
$b = a + 1\}$ be the set of end-to-end simple paths through T.

-continued

Algorithm 1 Find-Backbones: T → B

Let len: $p \in P \to R \equiv \sum_{\substack{p_a, p_b \in p, \\ b=a+1}} \begin{Bmatrix} \sqrt{2}, & \text{if } |p_{a_x} - p_{b_x}| = 1 \wedge |p_{a_y} - p_{b_y}| = 1; \\ 1, & \text{otherwise} \end{Bmatrix}$ be the length function that sums the straight line pixel transition distances in an end-to-end simple path through T.

Let $B = \left\{ b \mid b \in P, \text{len}(b) = \max_{p \in P} \text{len}(p) \right\}$ be the set of longest end-to-end simple paths through T (i.e. a backbone contours).

1: pid ← 0
2: S ← ∅
3: $p_{init}$.len ← 0
4: $p_{init}$.pix ← ∅
5: $P_{e_1} \leftarrow \{p_{init}\}$
6: Find-Paths-From ($e_1 \in \epsilon$, ∅,T, $\vec{P}_{e_1}$, $\vec{S}$, $\vec{pid}$, pid)
7: pid ← pid + 1

8: $B_{e_1} \leftarrow \left\{ b \mid b \in P_{e_1}, \text{len}(b) = \max_{p \in P_{e_1}} \text{len}(p) \right\}$ 9: $e_2 \leftarrow$ b.pix[last], where $b \in B_{e_1}$
10: S ← θ
11: $p_{init}$.len ← 0
12: $p_{init}$.pix ← ∅
13: $P_{e_2} \leftarrow \{p_{init}\}$
14: Find-Paths-From ( $e_2$, 0, T, $\vec{P}_{e_2}$, $\vec{S}$, $\vec{pid}$, pid)

15: $B_{e_2} \leftarrow \left\{ b \mid b \in P_{e_2}, \text{len}(b) = \max_{p \in P_{e_2}} \text{len}(p) \right\}$ 16: $B \leftarrow \left\{ b \mid b \in B_{e_1} \cup B_{e_2}, \text{len}(b) = \max_{b' \in B_{e_1} \cup B_{e_2}} \text{len}(b') \right\}$ 17: return B Algorithm 2 FIND-PATHS-FROM:
pix × dir × T × $\vec{P}$ × $\vec{S}$ × $\vec{pid}$ × root_pid → ∅

Let di: $p_a, p_b \in p \in P \to \{N, S, E, W, NW, NE, SW, SE\} \equiv$ $\begin{Bmatrix} N, & \text{if } dx = 0 \wedge dy = 1; \\ S, & \text{if } dx = 0 \wedge dy = -1; \\ E, & \text{if } dx = 1 \wedge dy = 0; \\ W, & \text{if } dx = -1 \wedge dy = 0; \\ NW, & \text{if } dx = 1 \wedge dy = 1; \\ NE, & \text{if } dx = 1 \wedge dy = 1; \\ SW, & \text{if } dx = -1 \wedge dy = -1; \\ SE, & \text{if } dx = 1 \wedge dy = -1. \end{Bmatrix}$ be the direction function that gives the orientation of $p_b$ with respect to $p_a$.

1: if pix $\in \vec{S}$ then
2:   return
3: $\vec{S} \leftarrow \vec{S} \cup \{pix\}$
4: if dir $\in \{N, S, E, W\}$ then
5:   $\vec{P}$[root_pid].len ← $\vec{P}$[root_pid].len + 1
6: else if dir $\in \{NE, NW, SE, SW\}$ then
7:   $\vec{P}$[root_pid].len ← $\vec{P}$[root_pid].len + $\sqrt{2}$
8: $\vec{P}$[root_pid].pix ← $\vec{P}$[root_pid].pix ∪ {pix}
9: N ← ∅

-continued

Algorithm 2 FIND-PATHS-FROM:
pix × dir × T × $\vec{P}$ × $\vec{S}$ × $\vec{pid}$ × root_pid → ∅

10: for dx $\in \{-1, 0, 1\}$ do
11:   for dy $\in \{-1, 0, 1\}$ do
12:     if dx = 0 $\wedge$ dy = 0 then
13:       continue
14:     n_pix ← ($pix_x$ + dx, $pix_y$ + dy)
15:     if n_pix $\in \vec{S}$ then
16:       continue
17:     n.pix ← n_pix
18:     n.dir ← dir (dx, dy)
19:     N ← N ∪ {n}
20: for n $\in$ N do
21:   if |N| > 1 then
22:     $\vec{pid} \leftarrow \vec{pid}$ + 1
23:     $\vec{P}$[last + 1] ← $\vec{P}$[root_pid]
24:   Find-Paths-From(n.pix, n.dir, T, $\vec{P}$, $\vec{S}$, $\vec{pid}$, pid)
25: if |N| > 1 then
26:   $\vec{P}$[root_pid] ← ∅
27: return AFM Explorer Length Estimation Pipeline AFM Explorer uses the length estimation pipeline schematically presented in FIG. 3. The steps are outlined below.

Initial Estimation Using Straight Line Segments

Let B be the set of all backbone pixel vectors in the image. After image processing, the initial estimate of contour length was computed for each $\vec{b} \in B$ as the sum of its consecutive pixel-to-pixel straight line segments, given by:

$$L_{LS}(\vec{b}) = \sum_{\substack{b_i, b_j \in \vec{b}, \\ j=i+1}} \left\{ \begin{array}{ll} \sqrt{2}, & \text{if } |b_{i_x} - b_{j_x}| = 1 \wedge |b_{i_y} - b_{j_y}| = 1; \\ 1, & \text{otherwise.} \end{array} \right\}$$

One then admits a subset $B' \subset B$ of backbone pixel vectors, where each $\vec{b}' \in B'$ meets two criteria: (1) its length is between min and max, set to some mode-dependent values, described below; and (2) it does not intersect with another backbone, according to a simple length heuristic.

Secondary Estimation Using Cubic Spline Fitting

Then, for each $\vec{b}' \in B'$, we computed a sequence of cubic splines fitted to each consecutive 5-pixel subsequence, where the last pixel of a given subsequence is the first pixel of the next (i.e. all subsequences share one extremity pixel). A tailing subsequence, $\vec{b}'_t$, having p<5 pixels is handled by fitting a cubic spline to the subsequence formed by prepending to $\vec{b}'_t$ the prior 5−p pixels, then counting the spline's length from its closest approach to the first and last pixels in $\vec{b}'_t$. The resulting summed length of the cubic splines gives the second estimate of contour length, given by:

$$L_{CS} = \sum_{i=1}^{k} CS\mathcal{L}_i,$$

where k is the number of cubic splines that fit the $|\vec{b}'|$ pixels, given by $$k = \left\lfloor \frac{|\vec{b}'| - 1 + \delta}{4} \right\rfloor, \delta < 4,$$

and $$CS\mathcal{L}_i = t_{i_\beta} - t_{i_\alpha},$$

where $\alpha$ and $\beta$ are the first and last pixels, in the $i^{th}$ 5-pixel subsequence being fit with a cubic spline, and $t_{i_\alpha}$ and $t_{i_\beta}$ are the respective values of the length parameter t that satisfy, respectively $$\frac{d}{dt}\left[\sqrt{(\alpha_x - x(t))^2 + (\alpha_y - y(t))^2}\right]\bigg|_{t=t_{i_\alpha}} = 0$$

and $$\frac{d}{dt}\left[\sqrt{(\beta_x - x(t))^2 + (\beta_y - y(t))^2}\right]\bigg|_{t=t_{i_\beta}} = 0,$$

(i.e., the values of t where the cubic spline makes its closes approach to the first and last pixels), where $$x(t) = \alpha_3 t^3 + \alpha_2 t^2 + \beta_1 t + \alpha_0$$

and $$y(t) = b_3 t^3 + b_2 t^2 + b_1 t + b_0$$

form the parametric equations of the cubic spline, and are solutions to the respective overdetermined systems $$\begin{bmatrix} t_1^3 & t_1^2 & t_1 & 1 \\ t_2^3 & t_2^2 & t_2 & 1 \\ t_3^3 & t_3^2 & t_3 & 1 \\ t_4^3 & t_4^2 & t_4 & 1 \\ t_5^3 & t_5^2 & t_5 & 1 \end{bmatrix} \begin{bmatrix} \alpha_3 \\ \alpha_2 \\ \alpha_1 \\ \alpha_0 \end{bmatrix} = \begin{bmatrix} x_1 \\ x_2 \\ x_3 \\ x_4 \\ x_5 \end{bmatrix} \Leftrightarrow T\vec{\alpha} = \vec{x}$$

and $$\begin{bmatrix} t_1^3 & t_1^2 & t_1 & 1 \\ t_2^3 & t_2^2 & t_2 & 1 \\ t_3^3 & t_3^2 & t_3 & 1 \\ t_4^3 & t_4^2 & t_4 & 1 \\ t_5^3 & t_5^2 & t_5 & 1 \end{bmatrix} \begin{bmatrix} b_3 \\ b_2 \\ b_1 \\ b_0 \end{bmatrix} = \begin{bmatrix} y_1 \\ y_2 \\ y_3 \\ y_4 \\ y_5 \end{bmatrix} \Leftrightarrow T\vec{b} = \vec{y}$$

where $$\begin{bmatrix} t_1 \\ t_2 \\ t_3 \\ t_4 \\ t_5 \end{bmatrix} = \begin{bmatrix} L_{LS}([(x_1, y_1)]) \\ L_{LS}([(x_1, y_1) \; (x_2, y_2)]) \\ L_{LS}([(x_1, y_1) \; (x_2, y_2) \; (x_3, y_3)]) \\ L_{LS}([(x_1, y_1) \; (x_2, y_2) \; (x_3, y_3) \; (x_4, y_4)]) \\ L_{LS}([(x_1, y_1) \; (x_2, y_2) \; (x_3, y_3) \; (x_4, y_4) \; (x_5, y_5)]) \end{bmatrix}$$

and thus, $\vec{\alpha}$ and $\vec{b}$ can respectively be evaluated analytically by $$\vec{\alpha} = (T^T T)^{-1} T^T \vec{x}$$

and $$\vec{b} = (T^T T)^{-1} T^T \vec{y},$$

for an arbitrary 5-pixel subsequence.

The pipeline has three phases (or rather, operates in two distinct modes): train and apply. These are shown schematically in FIG. 3, and are described in detail below.

FIG. 3: AFM Explorer length estimation pipeline. Length estimation undergoes two phases of processing: (I) train the coefficients of a simple linear regression model on a flexibly sized set of calibrating molecule backbones, each with its cubic spline length and set of features, and (II) apply the trained model to correct the cubic spline length of novel backbones according to their individual features.

Train

When the application runs in train mode, each admissible backbone pixel vector, $\vec{b}' \in B'$, its cubic spline contour length estimate, $L_{CS}(\vec{b}')$ and its computed feature values (described below) form the data of a possibly overdetermined linear system. We assume the images used to train represent a monodisperse set of molecules having known theoretical length C. Accordingly, the values of min and max should reflect reasonable expectations for a spread of $L_{LS}(\vec{b}')$ values observed for these molecules. For example, in one of our experiments, we trained on images of monodisperse cDNAs having theoretical length 75 nm. Since we have empirically observed at least +10 nm translation of the mean due to systematic errors, we chose a mean of 85 nm and a spread of ±15 nm—thus, we set min to 70 nm and max to 100 nm.

CLAIM 1. Since each fit cubic spline locally minimizes the sum of squares error in its 5-pixel window, then our conjoined cubic spline fitting across the whole backbone contour is a best linear unbiased estimator (BLUE), and any further correction to the estimate is systematic error, $$\mathcal{L} - L_{CS}(\vec{b}') = \epsilon_{\vec{b}'},$$

That can be derived from backbone-length-dependent feature values we learn from the data.

CLAIM 2. Given an increasingly large training sample and an increasingly rich feature set, our estimator will approach the optimal estimator.

The features. Five features were considered for the modeling of the systematic error. Given $\vec{b}' \in B'$:

DEFINITION 1. The number of horizontal pixel pairs, $n_{horz}$:

$$\vec{b}' \to N \equiv \sum_{\substack{b_i, b_j \in \vec{b}', \\ j=i+1}} \begin{cases} 1, & \text{if } |b_{i_x} - b_{j_x}| = 1 \wedge |b_{i_y} - b_{j_y}| = 0; \\ 0, & \text{otherwise.} \end{cases}$$

DEFINITION 2. The number of vertical pixel pairs, $n_{vert}$:

$$\vec{b}' \to N \equiv \sum_{\substack{b_i, b_j \in \vec{b}', \\ j=i+1}} \begin{cases} 1, & \text{if } |b_{i_x} - b_{j_x}| = 0 \wedge |b_{i_y} - b_{j_y}| = 1; \\ 0, & \text{otherwise.} \end{cases}$$

DEFINITION 3. The number of diagonal pixel pairs, $n_{diag}$:

$$\vec{b}' \to N \equiv \sum_{\substack{b_i, b_j \in \vec{b}', \\ j=i+1}} \begin{cases} 1, & \text{if } |b_{i_x} - b_{j_x}| = 1 \wedge |b_{i_y} - b_{j_y}| = 1; \\ 0, & \text{otherwise.} \end{cases}$$

DEFINITION 4. The number of perpendicular pixel triplets, $n_{perp}$:

$$\vec{b}' \to$$

$$N \equiv \sum_{\substack{b_i, b_j, b_k \in \vec{b}', \\ j=i+1, \\ k=j+1}} \begin{cases} 1, & \text{if } \begin{cases} \left\{\begin{array}{l}(|b_{i_x} - b_{j_x}| = 1 \wedge |b_{i_y} - b_{j_y}| = 0) \\ \wedge \\ (|b_{j_x} - b_{k_x}| = 0 \wedge |b_{j_y} - b_{k_y}| = 1)\end{array}\right\} \\ \vee \\ \left\{\begin{array}{l}(|b_{i_x} - b_{j_x}| = 0 \wedge |b_{i_y} - b_{j_y}| = 1) \\ \wedge \\ (|b_{j_x} - b_{k_x}| = 1 \wedge |b_{j_y} - b_{k_y}| = 0)\end{array}\right\} \\ \vee \\ \left\{\begin{array}{l}(|b_{i_x} - b_{j_x}| = 1 \wedge |b_{i_y} - b_{j_y}| = 1) \\ \wedge \\ (|b_{j_x} - b_{k_x}| = 1 \wedge |b_{j_y} - b_{k_y}| = 1)\end{array}\right\} \end{cases} \\ 0, & \text{otherwise.} \end{cases}$$

DEFINITION 5. The mean backbone thickness, $n_{tkav}$:

$$\vec{b}' \to R \equiv \frac{1}{|\vec{b}'|} \sum_{b \in \vec{b}'} M(b),$$

where $$M: b \to R \equiv \min \begin{cases} \sum_{\left\{\begin{array}{l}p|p_x=b_x-1,b_x-2,\ldots \\ \wedge p_y=b_y \\ \wedge I_{bin}(p)=255\end{array}\right\}} 1 + \\ \sum_{\left\{\begin{array}{l}p|p_x=b_x+1,b_x+2,\ldots \\ \wedge p_y=b_y \\ \wedge I_{bin}(p)=255\end{array}\right\}} 1, \\ \sum_{\left\{\begin{array}{l}p|p_x=b_x \\ \wedge p_y=b_y-1,b_y-2,\ldots \\ \wedge I_{bin}(p)=255\end{array}\right\}} 1 + \\ \sum_{\left\{\begin{array}{l}p|p_x=b_x \\ \wedge p_y=b_y+1,b_y+2,\ldots \\ \wedge I_{bin}(p)=255\end{array}\right\}} 1, \\ \sum_{\left\{\begin{array}{l}p|p_x=b_x-1,b_x-2,\ldots \\ \wedge p_y=b_y-1,b_y-2,\ldots \\ \wedge I_{bin}(p)=255\end{array}\right\}} \sqrt{2} + \\ \sum_{\left\{\begin{array}{l}p|p_x=b_x+1,b_x+2,\ldots \\ \wedge p_y=b_y+1,b_y+2,\ldots \\ \wedge I_{bin}(p)=255\end{array}\right\}} \sqrt{2}, \\ \sum_{\left\{\begin{array}{l}p|p_x=b_x-1,b_x-2,\ldots \\ \wedge p_y=b_y+1,b_y+2,\ldots \\ \wedge I_{bin}(p)=255\end{array}\right\}} \sqrt{2} + \\ \sum_{\left\{\begin{array}{l}p|p_x=b_x+1,b_x+2,\ldots \\ \wedge p_y=b_y-1,b_y-2,\ldots \\ \wedge I_{bin}(p)=255\end{array}\right\}} \sqrt{2} \end{cases}$$

gives the minimum of four pairs of linear distances that radiate in opposite directions from the origin at pixel b until they reach the edge of the binary object, thereby covering the 8 cardinal directions connecting the pixels in the binary object, where $I_{bin}: p \to \{0, 255\}$ gives the intensity value for pixel p in the binary image.

The Model.

We trained a linear regression model on q>5 calibrating molecule backbones, $\vec{b}' \in B'$, having known theoretical length $\mathcal{L}$, using values from these 5 features: $\{n_{horz}, n_{vert}, n_{diag}, n_{perp}, n_{tkav}\}$, giving:

$$\begin{bmatrix} n_{horz}(\vec{b}'_1) & n_{vert}(\vec{b}'_1) & n_{diag}(\vec{b}'_1) & n_{perp}(\vec{b}'_1) & n_{tkav}(\vec{b}'_1) \\ n_{horz}(\vec{b}'_2) & n_{vert}(\vec{b}'_2) & n_{diag}(\vec{b}'_2) & n_{perp}(\vec{b}'_2) & n_{tkav}(\vec{b}'_2) \\ n_{horz}(\vec{b}'_3) & n_{vert}(\vec{b}'_3) & n_{diag}(\vec{b}'_3) & n_{perp}(\vec{b}'_3) & n_{tkav}(\vec{b}'_3) \\ n_{horz}(\vec{b}'_4) & n_{vert}(\vec{b}'_4) & n_{diag}(\vec{b}'_4) & n_{perp}(\vec{b}'_4) & n_{tkav}(\vec{b}'_4) \\ n_{horz}(\vec{b}'_5) & n_{vert}(\vec{b}'_5) & n_{diag}(\vec{b}'_5) & n_{perp}(\vec{b}'_5) & n_{tkav}(\vec{b}'_5) \\ & & \dots & & \\ n_{horz}(\vec{b}'_q) & n_{vert}(\vec{b}'_q) & n_{diag}(\vec{b}'_q) & n_{perp}(\vec{b}'_q) & n_{tkav}(\vec{b}'_q) \end{bmatrix} \begin{bmatrix} \alpha_1 \\ \alpha_2 \\ \alpha_3 \\ \alpha_4 \\ \alpha_5 \end{bmatrix} = \begin{bmatrix} l_1 \\ l_2 \\ l_3 \\ l_4 \\ l_5 \\ \dots \\ l_q \end{bmatrix} \Leftrightarrow N\vec{\alpha} = \vec{l},$$

where N is the q×5 feature matrix, $\vec{\alpha}$ is the correction coefficient 5-vector to solve for, and $\vec{l}$ is the length estimate error q-vector [..., $(\mathcal{L} - L_{CS}(\vec{b}'_i))$, ...], where i=1, ..., q. The model has the analytic solution:

$$\vec{\alpha} = (N^T N)^{-1} N^T \vec{l}.$$

Figure 4A:
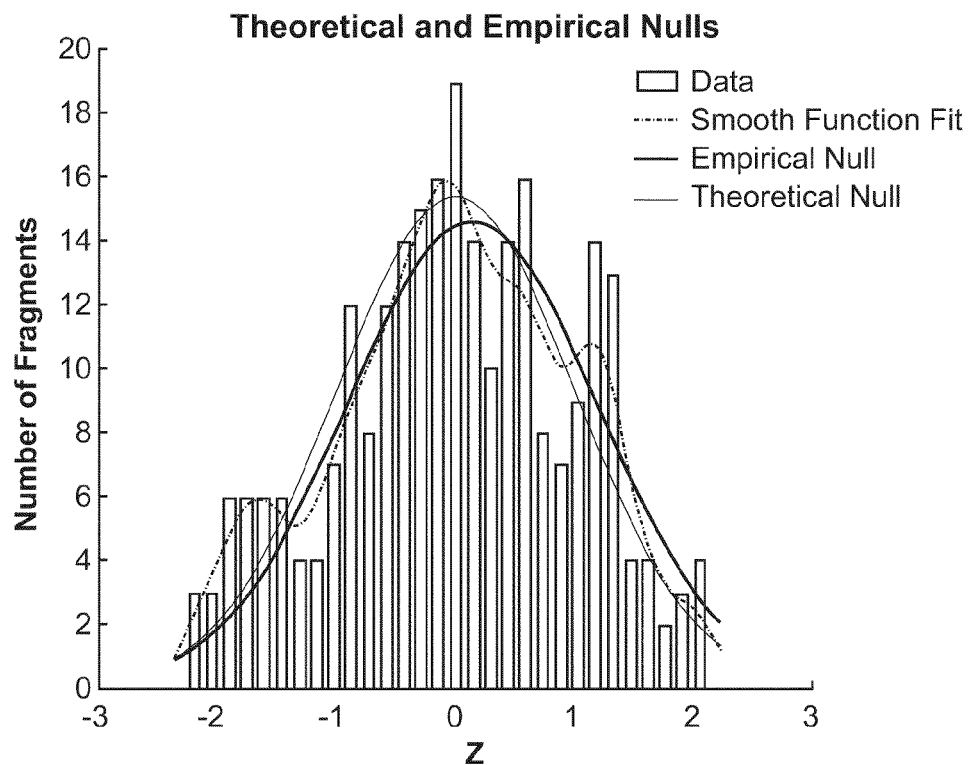
FIGS. 4A and 4B depict: theoretical and empirical null distributions of $L_{CS}$ values of Train (FIG. 4A); and local false discovery rate (FDR) curves derived from the theoretical and empirical null distributions of $L_{CS}$ values of Train, with respect to $f(Z)$.
Figure 4B:
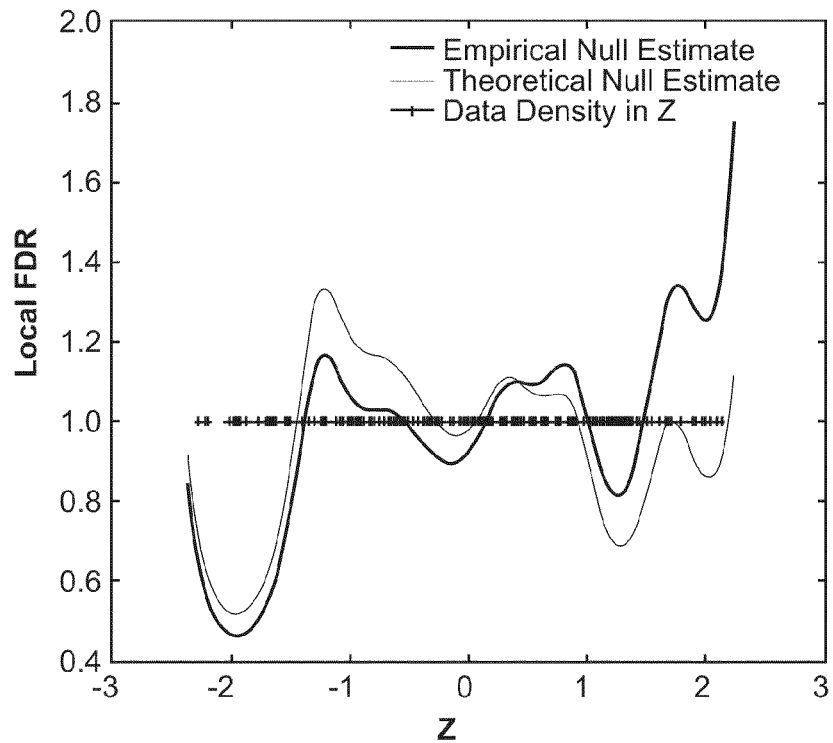

This formulation of the estimator, $\mathcal{L}'_T$ assumes all fragments, i.e., their associated feature values, have equal weight, owing to their equivalent validity as observations. However, such an assumption may be challenged on the grounds that upon taking into consideration the difference between the empirically measured null distribution and the actual shape of the distribution in $L_{CS}$ measurements, certain observations appear to be false positives, and others false negatives, a notion formally expressed as the false discovery rate (FDR). This suggests a weighted formulation of the error minimization problem, given by:

$$\min \|\vec{r}\|^2_W = \min \sum_{\vec{b}' \in B'} W(\vec{b}') r^2_{\vec{b}'},$$

where $$r_{\vec{b}'} = \mathcal{L} - L_{CS}(\vec{b}')$$

and
$W: R \to R$ is the local FDR weighting function. W was derived as follows. First the empirical null distribution $N_e(Z)$, of the training data in $L_{CS}$, was computed, where the distribution was taken from $L_{LS} \in [70, 100]$, by using a characteristic function approach. Next, a smooth function, $f(Z)$, was fit to the distribution using Matlab's ksdensity function with a kernel width of 0.2. Finally, obtaining the empirical local FDR is given by $$W(Z) = \frac{N_e(Z)}{f(Z)},$$

where Z is the Z-value of $L_{CS}$ (b') with respect to the theoretical null distribution, $N_t$, i.e., the standard normal fit, of the training data (see FIGS. 4A and 4B). The new weighted formulation of the estimator, $\mathcal{L}'_W$, is obtained by solving for a using the following Matlab pseudocode.

$N = \text{diag}(W)^* N;$ $\vec{l} = \text{diag}(W)^*(\mathcal{L} - L_{CS});$ $\vec{\alpha} = N/\vec{l};$ Once q≥5, the application will solve for $\vec{\alpha}$ and save its values to disk so that the trained model can be applied to test data.

FIG. 4A. Theoretical and empirical null distributions of $L_{CS}$ values of Train. N=263, $\mu_T$=85.49 nm, $\sigma_T$=6.73 nm, $c_{vT}$=0.08, $\mu_E$=86.39 nm, $\sigma_E$=7.09, $c_{vE}$=0.08 nm. FIG. 4B. Local FDR curves derived from the theoretical and empirical null distributions of $L_{CS}$ values of Train, with respect to $f(Z)$. The line at Local FDR=1 indicates the data density along the Z axis. The local FDR curve derived from the empirical null distribution is used to weight Train data during the training phase.

Apply. When the application is in apply mode, the model correction coefficients are locked—they are unadjusted from training—and are loaded from disk. In this mode, min and max are set to admit all molecules having a reasonable backbone contour length as first estimated by $L_{LS}$. So min=40 nm and max=1000 nm makes for a good range in most test situations. Then each $\vec{b}' \in B'$ obtains its final estimate, $\mathcal{L}' \in \{\mathcal{L}'_T, \mathcal{L}'_W\}$, from the correction function:

$C: B' \to R$ $: \vec{b}' \mapsto$ $\alpha_1 n_{horz}(\vec{b}') +$ $\alpha_2 n_{vert}(\vec{b}') +$ $\alpha_3 n_{diag}(\vec{b}') +$ $\alpha_4 n_{perp}(\vec{b}') +$ $\alpha_5 n_{tkav}(\vec{b}'),$ and is given by $\mathcal{L}(\vec{b}') = L_{CS}(\vec{b}') + C(\vec{b}').$ Experiments and Results An early version of AFM Explorer reported $L_{LS}$ for all existing fragments in the image. Comparing these automatically computed values with the length estimates of hand-drawn backbones (FIG. 5) gave us reason to believe that while an image processing pipeline can bring us close to the apparent length of DNAs and RNAs, more would be required. Namely, bridging the gap between apparent and true length would first require using a better length estimator (e.g. $L_{CS}$), and then from that, modeling the systematic error intrinsic to the problem.

Figure 5:
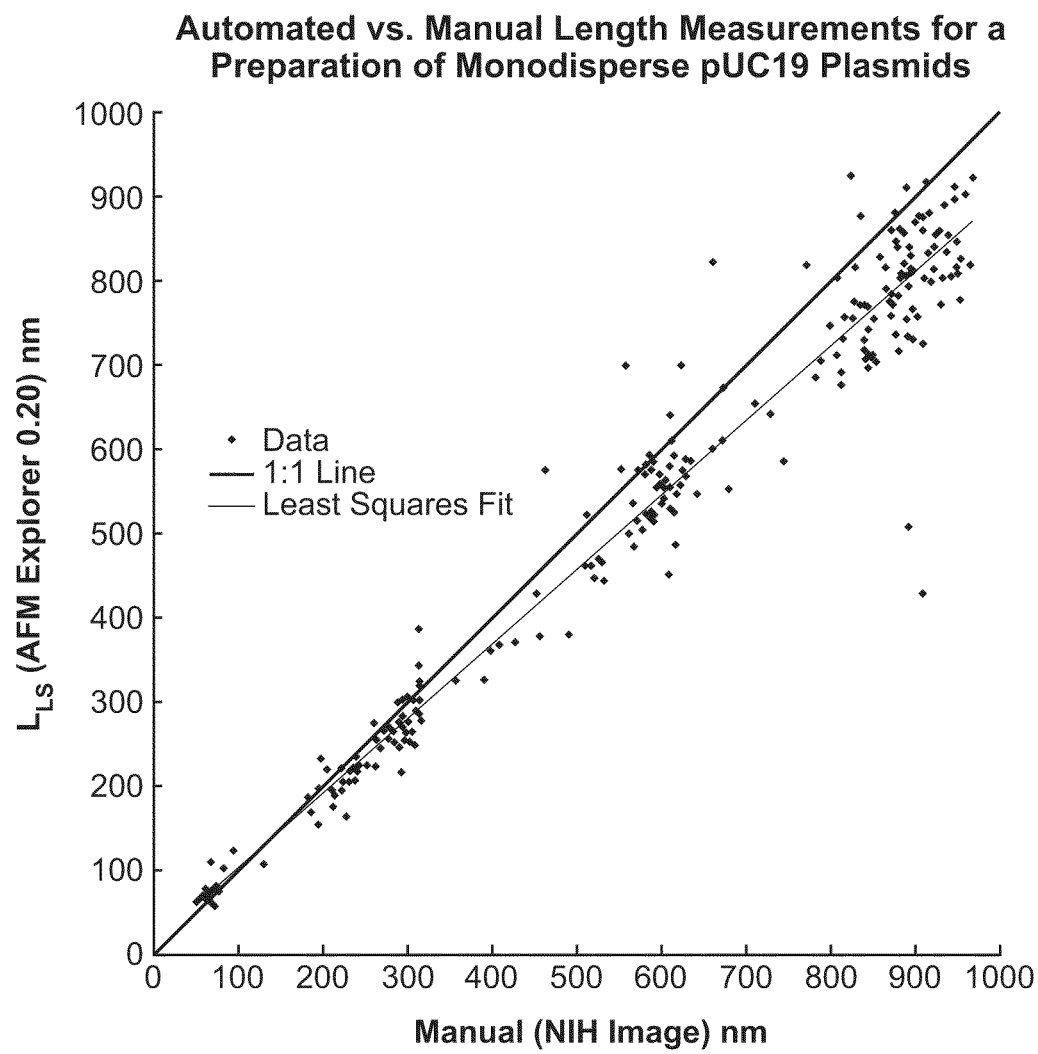
FIG. 5 depicts early comparative results.

FIG. 5. Early comparative results. Monodisperse pUC19 plasmids were linearized with EcoRI and digested with RsaI restriction enzymes. Fifty AFM images were taken of the resulting fragments, from which 245 fragments were selected and tagged. The lengths given by AFM Explorer (version 0.20, producing piecewise line segment lengths, $L_{CS}$) were compared against those of hand-drawn backbones using NIH Image. Note that as length increased, automatically computed $L_{LS}$ progressively underestimated fragment backbone length. Note too, the proximity of clustering (and theoretically given cleavage points induced by RsaI) around 90 (75), 275 (223), and 580 (584) nm; the clustering around 800 nm suggested failed digestion (an intrinsic experimental error).

Three regression models were tested, aside from the linear 5-feature model outlined in the Methods section. However, these were unsatisfactory because of overfitting during the training phase. These included: a quadratic 8-feature model, a linear 8-feature model, and a linear 6-feature model.

The experiments used three datasets:

1) 19 images comprising a monodisperse set of 1,034 admissible ($L_{LS} \in [70, 100]$ nm) cDNAs having known theoretical length 75 nm;

2) 44 images comprising a monodisperse set of 15,477 admissible ($L_{LS} \in [10, 1000]$ nm) cDNAs having known theoretical length 223 nm, but blinded from the computation (hereafter "Test Unknowns A")

3) 101 images comprising a monodisperse set of 54,093 admissible {$L_{LS} \in [10, 1000]$ nm) cDNAs having known theoretical length 584 nm, but blinded from the computation (hereafter "Test Unknowns B").

Figures 6A, 6B:
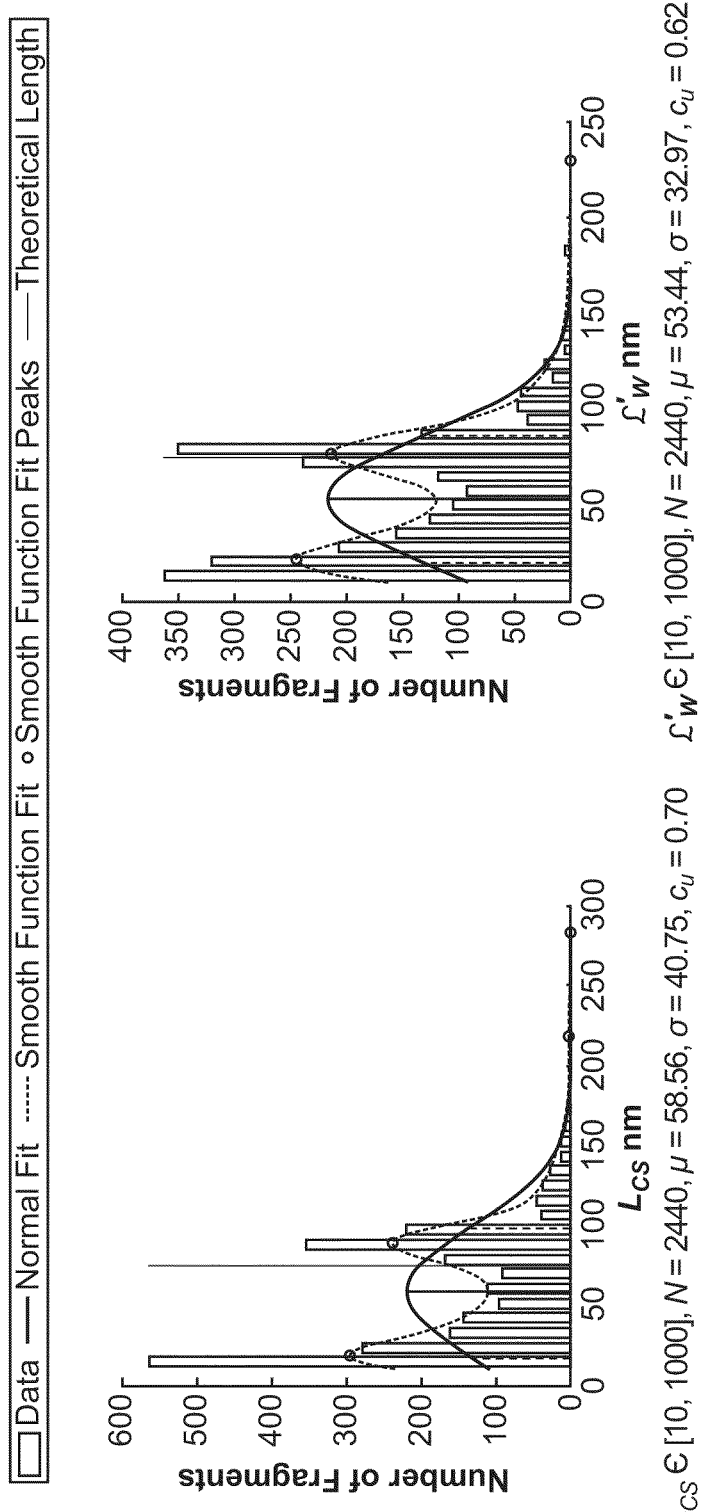
Figures 7A, 7B:
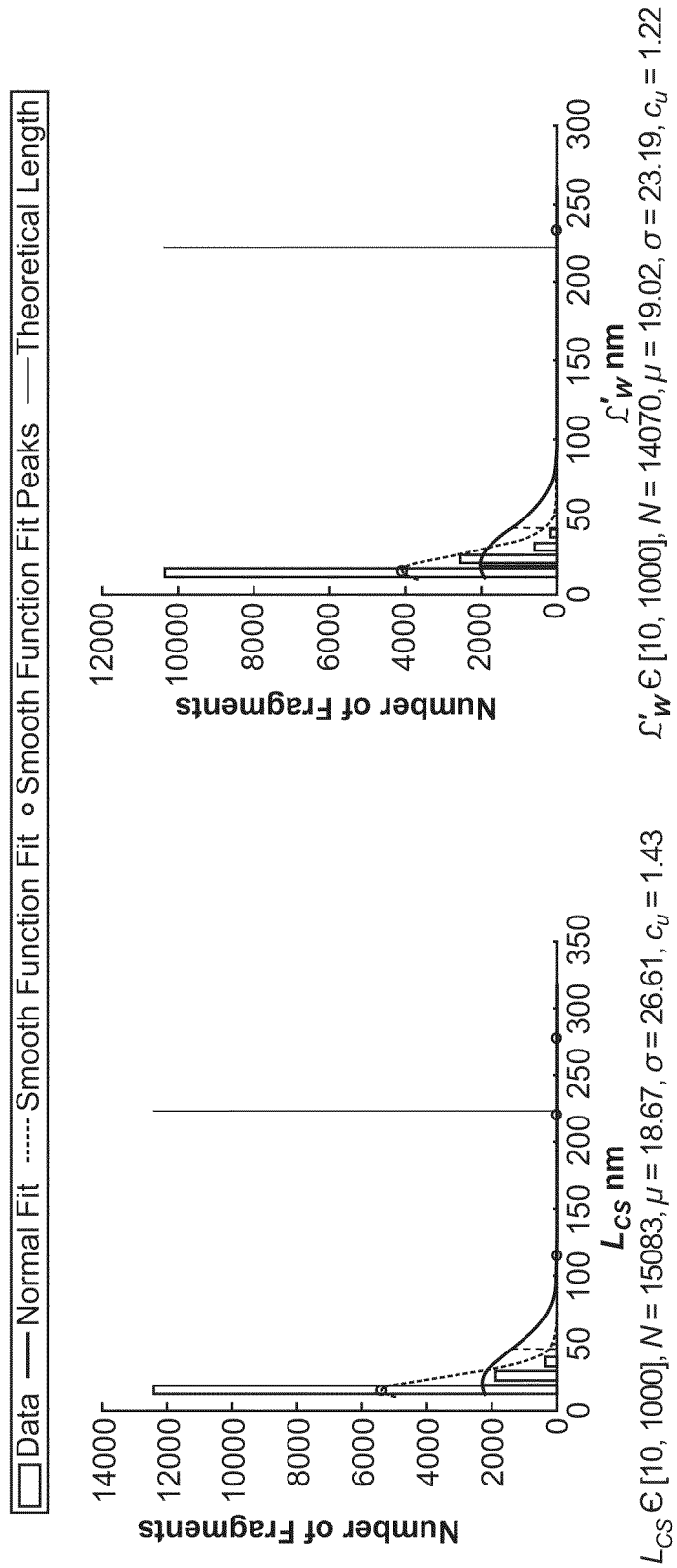
Figures 8A, 8B:
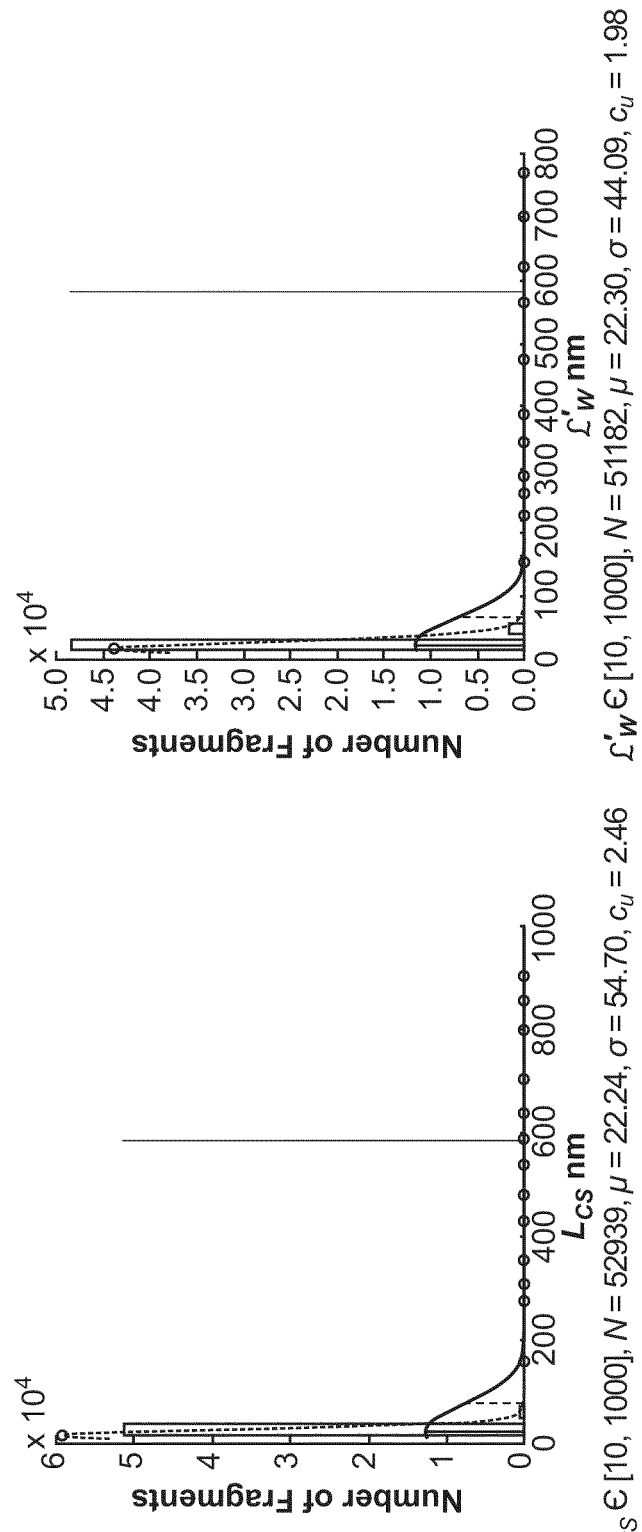

We partitioned the 19 images of the first dataset into the first 5 images for training (263 admissible cDNAs, $L_{LS} \in [70, 100]$, hereafter "Train") and the last 14 images for testing (2,440 admissible cDNAs, $L_{LS} \in [10, 1000]$, of which 771 have $L_{LS} \in [70, 100]$, hereafter "Test Knowns")—an arbitrary choice (see discussion below). Upon acquiring $L_{CS}$ and the 5-feature vector, n, for each of the 263 Train backbones, we trained our linear regression model by solving for the feature correction coefficients, a. In-sample standard deviations for our regular-trained, $L'_T$, and weighted-trained, $L'_W$, estimators are 5.30 nm and 4.67 nm, respectively, as compared with that of $L_{LS}$, which is 6.73 nm (see Table 2). We then tested $L'_T$ and $L'_W$ on the Test Knowns, Test Unknowns A, and Test Unknowns B datasets. The respective errors for these, and the distributions which gave rise to them, are plotted in FIGS. 6, 7, and 8.

where $L'_W \in [10, 1000]$ nm, is 19.02 nm, as one might expect from a set of 14,070 fragments, most of which are short noisy objects. The noise is a combination of electronic and vibration signal noise in the AFM system, and real particles or small bumps on the surface generated by the sample preparation—in general, these are never as long as even the smallest DNA molecules we are interested in measuring. To show the performance and sensitivity of the $L'_T$ and $L'_W$ estimators, we progressively narrowed the length regime for admissible fragments, tightening the focus on the areas of interest, around the known theoretical lengths of the monodisperse cDNAs in each dataset.

Looking at narrowest length regime selected by the best performing estimator, $L'_W$, it was found that $L'_W$ had μ equal to: 74.09 nm (σ=4.67 nm) for Train, 80.38 nm (σ=6.43 nm) for Test Knowns, 234.20 nm (σ=10.97 nm) for Test Unknowns A, and 553.61 nm (σ=23.60 nm) for Test Unknowns B.

TABLE 1

| | $L_{LS}$ [70, 100] N = 263 | | |
|---|---|---|---|
| | μ | σ | $c_v$ |
| $n_{horz}$ | 18.75 | 11.18 | 0.60 |
| $n_{vert}$ | 21.30 | 12.43 | 0.58 |
| $n_{diag}$ | 33.56 | 5.23 | 0.16 |
| $n_{perp}$ | 1.41 | 1.32 | 0.94 |
| $n_{tkav}$ | 5.12 | 1.32 | 0.26 |
| $L_{LS}$ | 85.45 | 6.73 | 0.08 |
| $L_{CS}$ | 85.49 | 6.73 | 0.08 |
| $L'_T$ | 74.63 | 5.30 | 0.07 |
| $L'_W$ | 74.09 | 4.67 | 0.06 |

Table 1 shows feature and length estimation results for Train. These statistics were gathered over 5 images, where the theoretical length of the cDNAs of interest is ζ=75 nm. Images were processed using the $$0.97 \frac{nm}{pix}$$

conversion factor.

TABLE 2

| | $L_{CS}$ | | | | | | | | | $L'_w$ | | | | | | | | |
|---|---|---|---|---|---|---|---|---|---|---|---|---|---|---|---|---|---|---|
| | [10, 1000] N = 2,440 | | | [50, 100] N = 989 | | | [70, 100] N = 771 | | | [10, 1000] N = 2,440 | | | [50, 100] N = 1,055 | | | [70, 100] N = 747 | | |
| | μ | σ | $c_v$ | μ | σ | $c_v$ | μ | σ | $c_v$ | μ | σ | $c_v$ | μ | σ | $c_v$ | μ | σ | $c_v$ |
| $n_{horz}$ | 12.93 | 11.61 | 0.90 | 18.12 | 9.86 | 0.54 | 19.81 | 9.73 | 0.49 | 12.92 | 11.61 | 0.90 | 18.50 | 9.74 | 0.53 | 20.26 | 9.55 | 0.47 |
| $n_{vert}$ | 14.50 | 13.49 | 0.93 | 19.59 | 10.88 | 0.56 | 20.64 | 11.25 | 0.55 | 14.50 | 13.48 | 0.93 | 20.60 | 11.41 | 0.55 | 22.07 | 11.71 | 0.53 |
| $n_{diag}$ | 23.00 | 16.57 | 0.72 | 32.23 | 6.97 | 0.22 | 34.67 | 5.44 | 0.16 | 23.00 | 16.57 | 0.72 | 33.35 | 7.36 | 0.22 | 36.45 | 5.63 | 0.15 |
| $n_{perp}$ | 1.08 | 1.23 | 1.14 | 1.41 | 1.21 | 0.86 | 1.52 | 1.23 | 0.81 | 1.08 | 1.23 | 1.14 | 1.48 | 1.26 | 0.85 | 1.63 | 1.28 | 0.79 |
| $n_{tkav}$ | 5.47 | 2.08 | 0.38 | 6.16 | 1.65 | 0.27 | 6.10 | 1.28 | 0.21 | 5.48 | 2.07 | 0.38 | 6.28 | 1.78 | 0.28 | 6.25 | 1.30 | 0.21 |
| $L_{LC}$ | 58.55 | 40.74 | 0.70 | 81.34 | 13.28 | 0.16 | 87.39 | 7.15 | 0.08 | 58.55 | 40.74 | 0.70 | 84.24 | 14.40 | 0.17 | 91.68 | 8.32 | 0.09 |
| $L_{CS}$ | 58.56 | 40.75 | 0.70 | 81.35 | 13.28 | 0.16 | 87.41 | 7.16 | 0.08 | 58.56 | 40.76 | 0.70 | 84.26 | 14.40 | 0.17 | 91.70 | 8.33 | 0.09 |
| $L'_T$ | 54.26 | 33.14 | 0.61 | 73.16 | 10.65 | 0.15 | 77.79 | 6.17 | 0.08 | 54.27 | 33.13 | 0.61 | 75.58 | 10.99 | 0.15 | 81.32 | 6.46 | 0.08 |
| $L'_W$ | 53.43 | 32.99 | 0.62 | 72.23 | 10.60 | 0.17 | 76.87 | 6.10 | 0.08 | 53.44 | 32.97 | 0.62 | 74.63 | 10.98 | 0.15 | 80.38 | 6.43 | 0.08 |

The feature and length estimation data for Train, Test Knowns, Test Unknowns A, and Test Unknowns B are summarized in Tables 1, 2, 3, and 4, respectively. Note that these are the values for all admissible fragments, with respect to the length measure and length regime indicated. For example, in Test Unknowns A, the mean value of $L'_W$, Table 2 shows feature and length estimation results for Test Knowns in narrowing length regimes (see FIGS. 6A-F). These statistics were gathered over 14 images, where the theoretical length of the cDNAs of interest is L=75 nm. Images were processed using the $$0.97 \frac{nm}{pix}$$

conversion factor.

TABLE 3

| | $L_{CS}$ | | | | | | | | | $L'_W$ | | | | | | | | |
|---|---|---|---|---|---|---|---|---|---|---|---|---|---|---|---|---|---|---|
| | [10, 1000] N = 15,083 | | | [100, 1000] N = 189 | | | [200, 1000] N = 139 | | | [10, 1000] N = 14,070 | | | [100, 1000] N = 177 | | | [200, 1000] N = 127 | | |
| | μ | σ | $c_v$ | μ | σ | $c_v$ | μ | σ | $c_v$ | μ | σ | $c_v$ | μ | σ | $c_v$ | μ | σ | $c_v$ |
| $n_{horz}$ | 5.67 | 7.94 | 1.40 | 63.84 | 26.00 | 0.41 | 74.19 | 20.55 | 0.28 | 5.75 | 8.18 | 1.42 | 66.05 | 25.27 | 0.38 | 75.86 | 19.67 | 0.26 |
| $n_{vert}$ | 2.88 | 6.41 | 2.22 | 49.74 | 22.78 | 0.46 | 56.73 | 20.83 | 0.37 | 3.02 | 6.60 | 2.18 | 51.73 | 22.01 | 0.43 | 57.35 | 20.53 | 0.36 |
| $n_{diag}$ | 7.47 | 10.40 | 1.39 | 91.22 | 27.16 | 0.30 | 105.66 | 12.76 | 0.12 | 7.72 | 10.72 | 1.39 | 94.54 | 24.72 | 0.26 | 107.95 | 10.40 | 0.10 |
| $n_{perp}$ | 0.79 | 1.15 | 1.46 | 5.56 | 3.09 | 0.56 | 6.35 | 3.01 | 0.47 | 0.78 | 1.16 | 1.48 | 5.66 | 3.09 | 0.55 | 6.52 | 2.99 | 0.46 |
| $n_{dkav}$ | 2.76 | 2.07 | 0.75 | 12.53 | 2.05 | 0.16 | 12.82 | 1.54 | 0.12 | 2.92 | 2.07 | 0.71 | 12.75 | 1.85 | 0.15 | 12.66 | 1.10 | 0.09 |
| $L_{LC}$ | 18.67 | 26.60 | 1.42 | 236.89 | 65.90 | 0.28 | 273.77 | 22.74 | 0.08 | 19.23 | 27.46 | 1.43 | 245.59 | 58.65 | 0.24 | 279.18 | 14.69 | 0.05 |
| $L_{CS}$ | 18.67 | 26.61 | 1.43 | 236.95 | 65.92 | 0.28 | 273.84 | 22.75 | 0.08 | 19.22 | 27.46 | 1.43 | 245.65 | 58.66 | 0.24 | 279.25 | 14.71 | 0.05 |
| $L'_T$ | 18.75 | 22.76 | 1.21 | 203.13 | 51.73 | 0.25 | 232.17 | 16.73 | 0.07 | 19.45 | 23.41 | 1.20 | 210.24 | 45.35 | 0.22 | 236.11 | 10.96 | 0.05 |
| $L'_W$ | 18.34 | 22.54 | 1.23 | 201.24 | 51.67 | 0.26 | 230.24 | 16.80 | 0.07 | 19.02 | 23.19 | 1.22 | 208.32 | 45.35 | 0.22 | 234.20 | 10.97 | 0.05 |

TABLE 4

| | $L_{CS}$ | | | | | | | | | $L'_W$ | | | | | | | | |
|---|---|---|---|---|---|---|---|---|---|---|---|---|---|---|---|---|---|---|
| | [10, 1000] N = 52,939 | | | [500, 1000] N = 305 | | | [500, 600] N = 77 | | | [10, 1000] N = 51,182 | | | [500, 1000] N = 205 | | | [500, 600] N = 194 | | |
| | μ | σ | $c_v$ | μ | σ | $c_v$ | μ | σ | $c_v$ | μ | σ | $c_v$ | μ | σ | $c_v$ | μ | σ | $c_v$ |
| $n_{horz}$ | 6.59 | 12.58 | 1.91 | 133.29 | 66.34 | 0.50 | 131.18 | 50.11 | 0.38 | 6.67 | 12.78 | 1.92 | 135.93 | 71.15 | 0.52 | 134.56 | 71.15 | 0.53 |
| $n_{vert}$ | 4.03 | 16.52 | 4.10 | 182.74 | 76.65 | 0.42 | 137.68 | 46.06 | 0.33 | 4.13 | 16.79 | 4.07 | 199.91 | 79.72 | 0.40 | 196.71 | 77.27 | 0.39 |
| $n_{diag}$ | 8.60 | 21.32 | 2.48 | 257.43 | 35.43 | 0.14 | 215.49 | 16.64 | 0.08 | 8.75 | 21.66 | 2.48 | 275.86 | 25.94 | 0.09 | 272.83 | 21.84 | 0.08 |
| $n_{perp}$ | 0.77 | 1.49 | 1.94 | 13.91 | 5.47 | 0.39 | 10.39 | 4.01 | 0.39 | 0.76 | 1.51 | 1.98 | 15.39 | 5.33 | 0.35 | 15.31 | 5.29 | 0.35 |
| $n_{dkav}$ | 3.25 | 2.10 | 0.65 | 10.45 | 1.48 | 0.14 | 10.98 | 1.84 | 0.17 | 3.36 | 2.07 | 0.62 | 10.26 | 1.31 | 0.13 | 10.30 | 1.29 | 0.13 |
| $L_{LC}$ | 22.24 | 54.69 | 2.46 | 664.16 | 79.57 | 0.12 | 560.17 | 28.17 | 0.05 | 22.62 | 55.58 | 2.46 | 708.95 | 52.33 | 0.07 | 700.31 | 33.35 | 0.05 |
| $L_{CS}$ | 22.24 | 54.70 | 2.46 | 664.32 | 79.56 | 0.12 | 560.32 | 28.21 | 0.05 | 22.62 | 55.59 | 2.46 | 709.11 | 52.29 | 0.07 | 700.47 | 33.29 | 0.05 |
| $L'_T$ | 22.32 | 43.58 | 1.95 | 528.11 | 59.47 | 0.11 | 450.64 | 23.38 | 0.05 | 22.80 | 44.24 | 1.94 | 561.75 | 38.38 | 0.07 | 555.19 | 23.59 | 0.04 |
| $L'_W$ | 21.84 | 43.42 | 1.99 | 526.49 | 59.52 | 0.11 | 448.92 | 23.30 | 0.05 | 22.30 | 44.09 | 1.98 | 560.17 | 38.38 | 0.07 | 553.61 | 23.60 | 0.04 |

Table 3 shows feature and length estimation results for Test Unknowns A in narrowing length regimes (see FIG. 7A-F). These statistics were gathered over 44 images, where the theoretical length of the cDNAs of interest is $\mathcal{L}$=223 nm. Images were processed using the $$0.97 \frac{nm}{pix}$$

conversion factor.

Table 4 shows feature and length estimation results for Test Unknowns B in narrowing length regimes (see FIG. 8A-F). These statistics were gathered over 101 images, where the theoretical length of the cDNAs of interest is L=584 nm. Images were processed using the $$0.97 \frac{nm}{pix}$$

conversion factor.

FIGS. 6A-F depict distributions of $L_{CS}$ (left column) and $L'_W$ (right column) for Test Knowns in narrowing length regimes (see Table 2). The theoretical length of the cDNAs of interest is L=75 nm. The smooth function fits, $f(L_{CS})$ and $f(L'_W)$, were created using Matlab's ksdensity function with a kernel width of 10.

FIGS. 7A-F depict distributions of $L_{CS}$ (left column) and $L'_W$ (right column) for Test Unknowns A in narrowing length regimes (see Table 3). The theoretical length of the cDNAs of interest is L=223 nm. The smooth function fits, $f(L_{CS})$ and $f(L'_W)$, were created using Matlab's ksdensity function with a kernel width of 10.

FIGS. 8A-F depict distributions of $L_{CS}$ (left column) and $L'_W$ (right column) for Test Unknowns B in narrowing length regimes (see Table 4). The theoretical length of the cDNAs of interest is L=584 nm. The smooth function fits, $f(L_{CS})$ and $f(L'_W)$, were created using Matlab's ksdensity function with a kernel width of 10.

In the problem described in this example, there are two principal sources of error: bias from the method of estimation (the extrinsic factors), and systematic error (the intrinsic factors). We have given a BLUE estimator for molecular backbone contour length, namely the piecewise cubic spline fitting measure, $L_{CS}$. But this gets us only part way to the answer, since systematic error underlies all such measurements. In our experiments, this was visible in the error distributions (FIGS. 6, 7, and 8), especially in Test Unknowns A and Test Unknowns B, where there was a clear divergence between $L_{CS}$ and the known theoretical lengths, C, of the cDNAs of interest. Various sources of systematic error can occur. We improved on $L_{CS}$ by training a linear regression model to estimate the systematic error and thereby correct Lcs, yielding a superior estimator, $C'_T$. By weighting the linear regression training based on computed local FDR, we created another estimator, C'w, that further improves performance. These estimators were trained on 5 features we developed for our method. One consequence of such a design is an inherent adaptability and extensibility: a researcher may compose any number and arrangement of features into the estimation.

Example 2: Detecting Identifying Feature Patterns in a Nucleic Acid

This example describes an exemplary embodiment of a method of detecting an identifying feature pattern in a nucleic acid.

FIG. 11A depicts a labeling method that allows cDNAs to be physically modified in close proximity to the sequence motifs recognized by nicking restriction endonucleases. This chemistry can be performed in solution, followed by deposition of the sample on a solid substrate for AFM imaging. The example demonstrated uses physical modification, followed by enzymatic addition of biotin and streptavidin at the modified site, for the purposes of rendering the site readily identifiable in an AFM image. However, depending upon the mode of AFM (or other) imaging, the step following the physical modification can be eliminated, or could be addition of a different moiety, or oligonucleotide binding, or additional physical modification, such as thermal or chemical denaturing for the nucleic acid duplex. This labeling process can be conducted with multiple nicking restriction endonucleases, applied in a serial fashion and labeled with different chemical moieties, to identify several different sequence motifs on a single molecule simultaneously, with the AFM. FIGS. 11B-11D depict the results of imaging and measuring surface-fixed cDNA molecules labeled in this fashion.

Figure 12A:
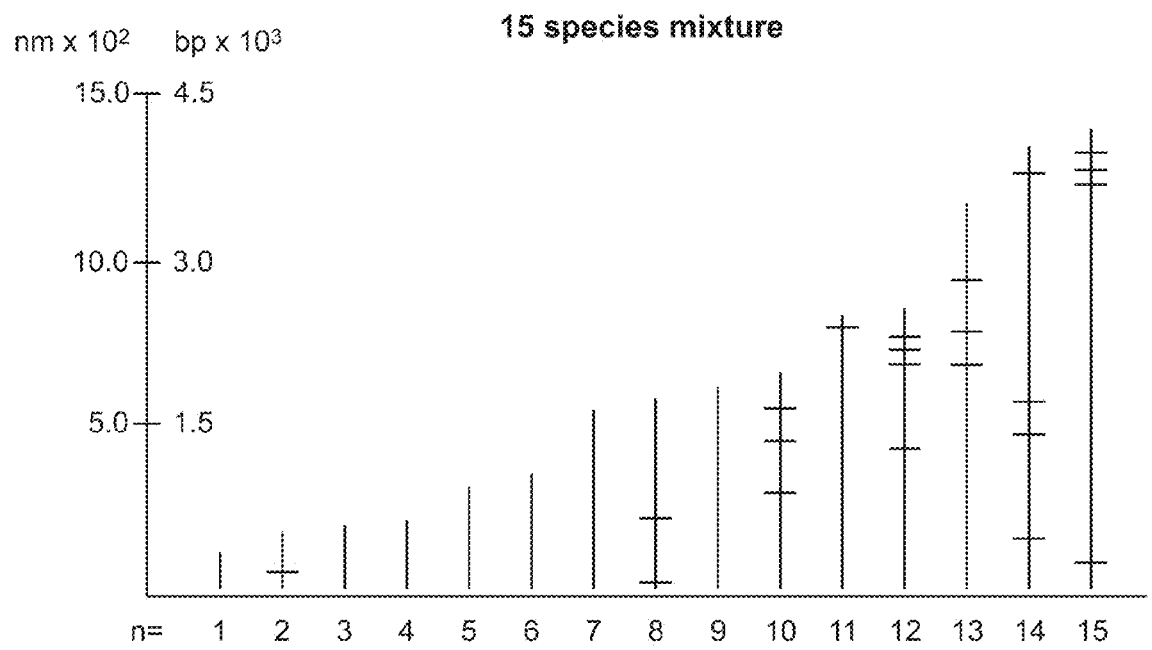
FIGS. 12A and 12B depict an exemplary embodiment of identifying feature pattern detection.
Figure 12B:
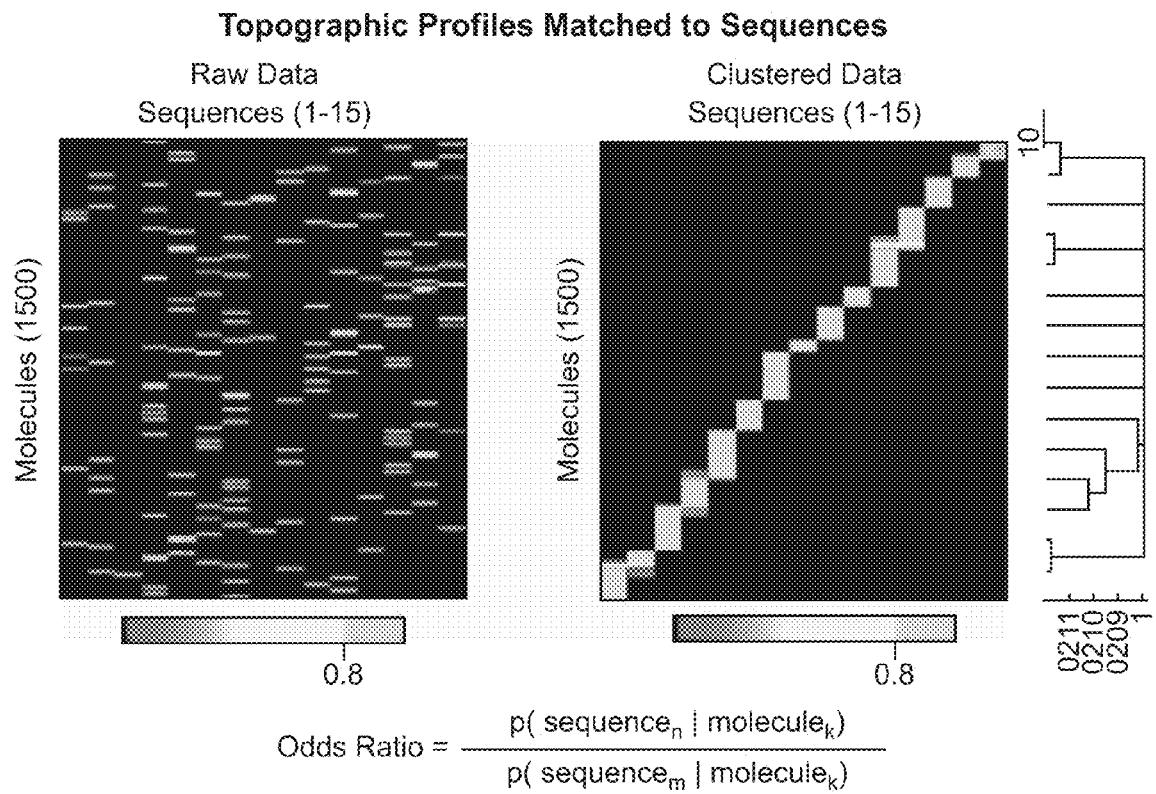

FIG. 12A depicts the schematic representation of 15 different species of cDNAs, where the red bars indicate the relative location of nicking restriction endonuclease labeling sites. The scale to the left shows the physical dimensions in both nanometers and base pairs. Panel (b) presents actual data derived from AFM analysis of 1,500 synthetic cDNA molecules, comprised of equal amounts of the 15 species given in FIG. 12A. To the left, each molecule is measured and converted to a pattern or "fingerprint" in the basis of the labels it contains and their spacing along the molecule backbone. These fingerprints are matched uniquely to the known patterns for the 15 species. In the figure, high confidence matches are displayed in green. To the right, these patterns can be clustered using standard algorithms so that all molecules belonging to a single species are grouped together in the dataset, and the morphologic similarity between species quantitatively determined via hierarchical clustering, displayed as a dendrogram plot on the far right.

Figure 13:
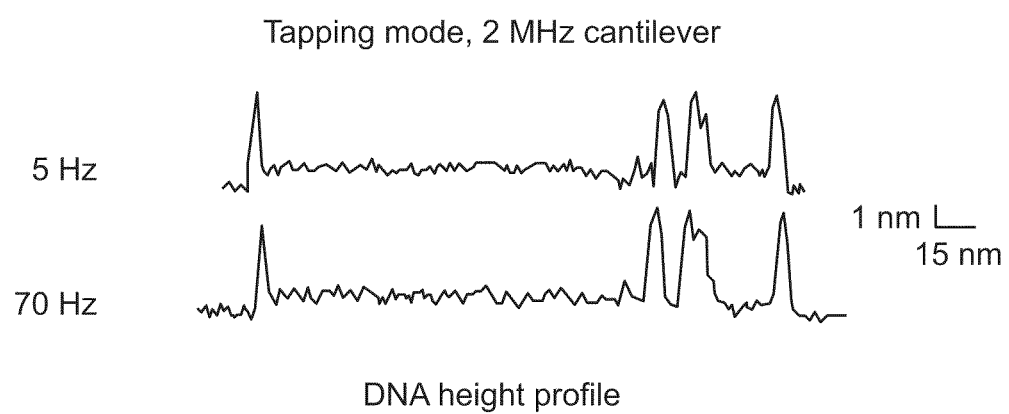
FIG. 13 depicts AFM-determined backbone profiles of a labeled molecule.

FIG. 13 depicts actual AFM-determined backbone profiles of a labeled molecule measured a "standard" imaging speeds ("5 hHz") and "fast" imaging speeds ("70 Hz"), enabled through the use of a high resonant frequency AFM cantilever (2 MHz). The analog traces show no significant distortion at higher speeds.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for determining a length of an immobilized test nucleic acid, the method comprising:
   a) immobilizing nucleic acids having known lengths on a surface of a support;
   b) generating a plurality of atomic force microscopy (AFM) images of the immobilized nucleic acids by scanning the immobilized nucleic acids with an AFM probe present in an AFM device;
   c) generating a plurality of coefficients for a polynomial function that provides a length estimate from the AFM images using a regression analysis;
   d) eliminating one or more of the coefficients to generate a set of correction coefficients;
   e) modifying the AFM probe by applying an external electrical current to the AFM probe, thereby generating an electrostatic potential at the nucleic acid-contacting end of the AFM probe to produce an electrostatically-modified AFM probe; and
   f) measuring the length of the immobilized test nucleic acid using the AFM device with the electrostatically-modified AFM probe.

2. The method of claim 1, wherein the measurement is a high-accuracy measurement having a coefficient of variation of less than 2%.

3. The method of claim 1, wherein the length is the distance between two or more identifying features of the nucleic acid.

4. The method of claim 3, wherein said measuring generates a pattern of identifying features.

5. The method of claim 4, further comprising comparing said pattern of identifying features to a reference pattern of identifying features of a known nucleic acid.

6. The method of claim 1, wherein the correction coefficients are generated from a weighted set of training set correction coefficients or by calibrating a nucleic acid or set of nucleic acids having a property of known measurement.

7. The method of claim 6, wherein training set correction coefficients are generated using one or more of: i) a feature relating to pixellation; ii) a physical feature of the nucleic acid; and iii) a mechanical feature of the nucleic acid.

8. The method of claim 7, wherein the mechanical feature is stiffness of the nucleic acid or an attractive force between the nucleic acid and the AFM probe.

9. The method of claim 8, wherein the mechanical feature is determined by measuring one or more of: i) a change in amplitude of the oscillating mode of the AFM probe; ii) a phase shift in the frequency of oscillation of the AFM probe; iii) a time-dependent average position of the AFM probe.

10. The method of claim 9, wherein the AFM probe is functionalized to modify the attractive force between the nucleic acid and the AFM probe.

11. The method of claim 10, wherein the nucleic acid-contacting end of the AFM probe is functionalized with an antibody, a hydrophilic group, a hydrophobic group, a group comprising an electrostatic charge, a probe nucleic acid that hybridizes to the nucleic acid being measured, a protein, a dye, or a magnetic material.

12. The method of claim 7, wherein the features include one or more of: i) the number of horizontal pixel pairs; ii) the number of vertical pixel pairs; iii) the number of diagonal pixel pairs; iv) the number of perpendicular pixel pairs; and v) the mean backbone thickness.

13. The method of claim 1, wherein the correction coefficients are weighted by a false discovery rate (FDR) control method based on an empirical Bayes method.

14. The method of claim 1, wherein a final set of correction coefficient yields an error term which is then applied to an initial estimate of length.

15. The method of claim 1, wherein the AFM probe is not functionalized.

* * * * *

UNITED STATES PATENT AND TRADEMARK OFFICE
CERTIFICATE OF CORRECTION

PATENT NO. : 9,995,766 B2
APPLICATION NO. : 12/817004
DATED : June 12, 2018
INVENTOR(S) : Reed et al.

Page 1 of 1

It is certified that error appears in the above-identified patent and that said Letters Patent is hereby corrected as shown below:

On the Title Page

Item (73), add the following as Assignee:
New York University, New York, NY (US)

Signed and Sealed this
Twenty-sixth Day of March, 2019

Andrei Iancu
*Director of the United States Patent and Trademark Office*